United States Patent
Sano et al.

(10) Patent No.: US 9,211,071 B2
(45) Date of Patent: Dec. 15, 2015

(54) CUFF FOR BLOOD PRESSURE INFORMATION MEASUREMENT DEVICE AND BLOOD PRESSURE INFORMATION MEASUREMENT DEVICE EQUIPPED WITH THE SAME

(75) Inventors: Yoshihiko Sano, Kyoto (JP); Reiji Fujita, Kyoto (JP); Takanori Nishioka, Kyoto (JP); Atsushi Kawano, Takarazuka (JP); Takahide Tanaka, Otsu (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 1129 days.

(21) Appl. No.: 13/229,930

(22) Filed: Sep. 12, 2011

(65) Prior Publication Data

US 2012/0004560 A1   Jan. 5, 2012

Related U.S. Application Data

(63) Continuation of application No. PCT/JP2010/052347, filed on Feb. 17, 2010.

(30) Foreign Application Priority Data

Mar. 12, 2009   (JP) ................................. 2009-059503

(51) Int. Cl.
*A61B 5/02* (2006.01)
*A61B 5/022* (2006.01)

(52) U.S. Cl.
CPC ............. *A61B 5/02233* (2013.01); *A61B 5/022* (2013.01)

(58) Field of Classification Search
CPC ........ A61B 5/02; A61B 5/022; A61B 5/0214; A44B 11/2588; A44B 11/08; B68B 3/22; B65H 23/198; B65H 23/16; B65H 23/12
USPC ............... 600/485–499; 606/202–203; 24/32, 24/127, 168, 194, 313, 325, 459; 254/223, 254/322, 357, 376, 391; 242/383.4, 383.5
See application file for complete search history.

(56) References Cited

U.S. PATENT DOCUMENTS 837,013 A * 11/1906 Wachter ............................ 54/54
4,337,553 A * 7/1982 Fischer ........................ 24/68 R
(Continued)

FOREIGN PATENT DOCUMENTS

JP   60-092039 U   6/1985
JP   S61-206546 U   12/1986
(Continued)

OTHER PUBLICATIONS

Patent Abstracts of Japan, Publication No. 2007-268052, Publication Date: Oct. 18, 2007, 1 page.
(Continued)

*Primary Examiner* — Navin Natnithithadha
*Assistant Examiner* — Eric Messersmith
(74) *Attorney, Agent, or Firm* — Osha Liang LLP

(57) ABSTRACT

A cuff for a sphygmomanometer includes an air bladder for compressing a living body, an exterior cover including the air bladder, and a fixing unit arranged in the exterior cover. A portion closer to an end of the exterior cover is inserted between a roller arranged in the fixing unit and a stopper, and is fixed by being pushed against the roller by the stopper. The roller is rotatable only in a direction of reducing the size of the annular portion of the exterior cover. Accordingly, the cuff for the sphygmomanometer has a simple configuration, is inexpensively manufactured, and easily carries out and stably reproduces attachment with respect to the upper arm.

6 Claims, 19 Drawing Sheets

(56) References Cited

U.S. PATENT DOCUMENTS

| | | |
|---|---|---|
| 2002/0099299 A1 | 7/2002 | Inagaki |
| 2006/0047206 A1* | 3/2006 | Sano et al. .................. 600/490 |

FOREIGN PATENT DOCUMENTS

| | | | | |
|---|---|---|---|---|
| JP | 63-056003 U | | 4/1988 | |
| JP | 63-117095 U | | 7/1988 | |
| JP | 63-125915 U | | 8/1988 | |
| JP | 02-37604 U | * | 3/1990 | ............. A61B 5/022 |
| JP | H02-37604 U | | 3/1990 | |
| JP | 2000-237150 A | | 9/2000 | |
| JP | 2002-209858 A | | 7/2002 | |
| JP | 2006-068318 A | | 3/2006 | |
| JP | 2007-075294 A | | 3/2007 | |
| JP | 2007-268052 A | | 10/2007 | |
| TW | I300707 B | | 9/2008 | |
| WO | 03/101290 A2 | | 12/2003 | |

OTHER PUBLICATIONS

Patent Abstracts of Japan, Publication No. 2002-209858, Publication Date: Jul. 30, 2002, 1 page.
Patent Abstracts of Japan, Publication No. 2006-068318, Publication Date: Mar. 16, 2006, 1 page.
Patent Abstracts of Japan, Publication No. 2007-075294, Publication Date: Mar. 29, 2007, 1 page.
Patent Abstracts of Japan, Publication No. 2000-237150, Publication Date: Sep. 5, 2000, 1 page.
International Search Report issued in PCT/JP2010/052347 mailed on Mar. 16, 2010 with English translation thereof, 4 pages.
Office Action issued Oct. 14, 2014, in related Taiwanese Application No. 099107029 (with translation) (14 pages).

* cited by examiner

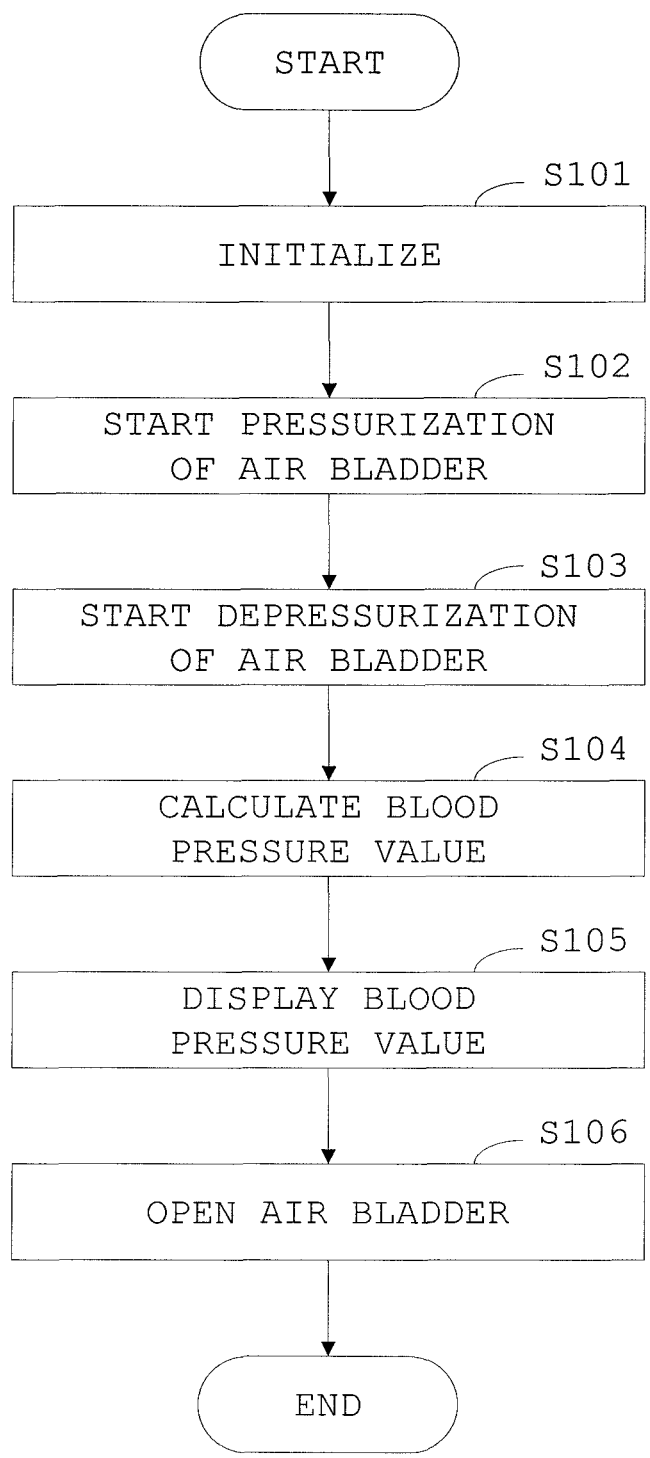

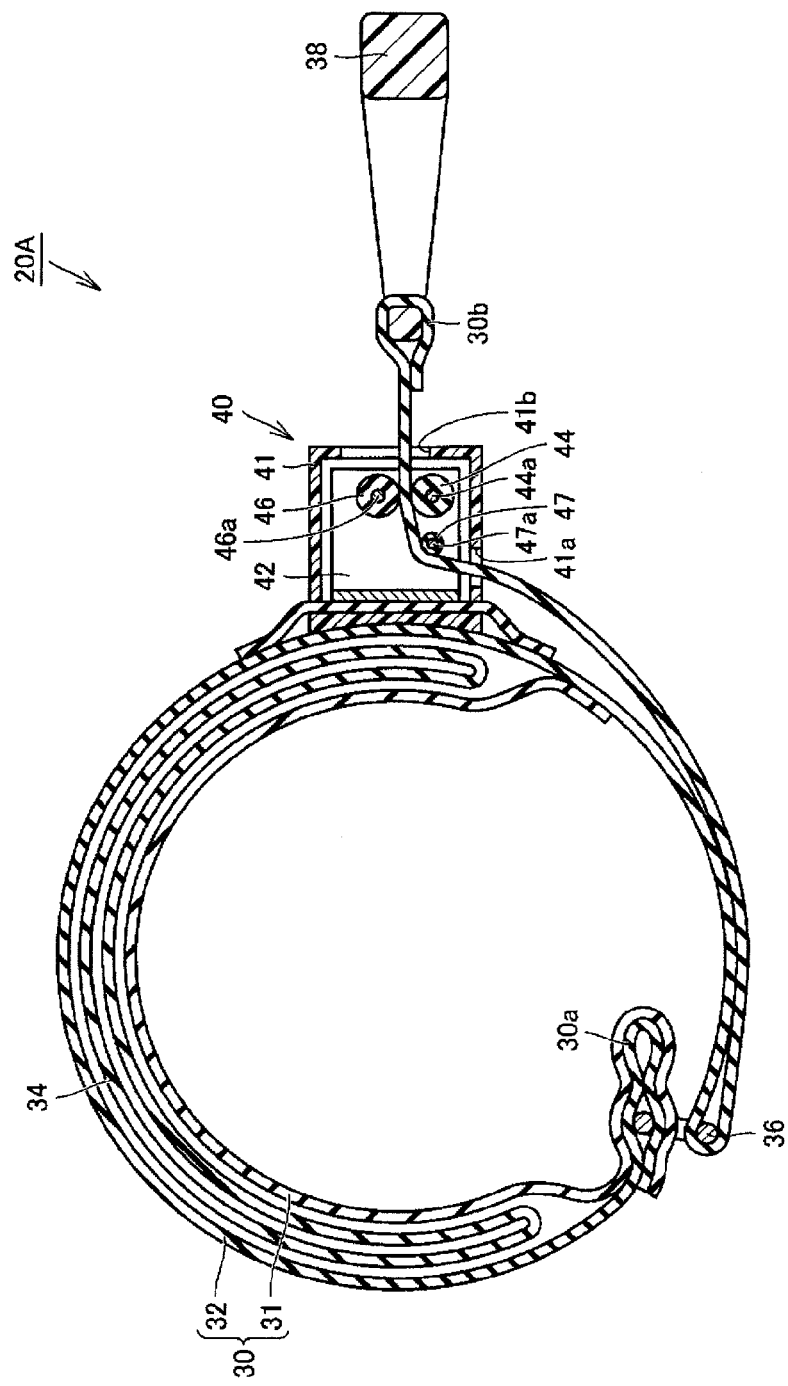

CUFF FOR BLOOD PRESSURE INFORMATION MEASUREMENT DEVICE AND BLOOD PRESSURE INFORMATION MEASUREMENT DEVICE EQUIPPED WITH THE SAME

TECHNICAL FIELD

The present invention relates to a cuff for a blood pressure information measurement device used by being attached to a site to be measured when measuring blood pressure information such as a blood pressure value, and a blood pressure information measurement device equipped with the same.

BACKGROUND ART

It is very important to acquire the blood pressure information of a subject in order to know about the health condition of the subject. In recent years, attempts have been made to capture the heart load and the change in hardness of the artery by acquiring the pulse wave of the subject, not limited to acquiring a systolic blood pressure value (maximum blood pressure value), a diastolic blood pressure value (minimum blood pressure value), and the like, which usability is widely recognized as a representative index of health management from the related art. The blood pressure information measurement device is a device for obtaining an index for health management based on the acquired blood pressure information, and further utilization in the field of early detection and prevention, treatment, or the like, of illnesses in the circulatory system is expected. The blood pressure information described above widely includes various information of the circulatory system such as a systolic blood pressure value, a diastolic blood pressure value, an average blood pressure value, a pulse wave, a pulse, and an AI (Augmentation Index) value.

A cuff for a blood pressure information measurement device (hereinafter also simply referred to as cuff) that includes a fluid bladder is generally used to measure the blood pressure information. The cuff refers to a band-shaped structure with an inner cavity that can be wrapped around one part of a living body, and it is used to measure the blood pressure information by injecting fluid such as gas or liquid into the inner cavity or discharging the fluid from the inner cavity to expand or contract the fluid bladder. For instance, in the blood pressure information measurement device (hereinafter also simply referred to as sphygmomanometer) for measuring the blood pressure value such as the systolic blood pressure value and the diastolic blood pressure value, the measurement of the blood pressure value is carried out by wrapping the cuff including the fluid bladder for compressing the artery around a body surface of the living body, and expanding and contracting the fluid bladder that is wrapped around the living body to capture the artery pressure pulse wave as a change in the inner pressure of the fluid bladder. The cuff used by being wrapped around the arm, in particular, is also called an arm band or a manchette.

The cuff is normally configured mainly by an air bladder serving as a fluid bladder, and a band-shaped exterior cover that includes the air bladder and that has an area fastener on the surface. The wide spread cuff conventionally has an annular form when, to an annular ring arranged at one end in a longitudinal direction of the exterior cover, the other end in the longitudinal direction of the exterior cover is inserted and folded back, where the blood pressure information can be measured by inserting the site to be measured to such annular portion of the exterior cover so that the cuff is wrapped around the site to be measured, and tightening the exterior cover and fixing it using the area fastener, so that the air bladder is wrapped around and fixed to the site to be measured (see e.g., FIG. 2 of Japanese Unexamined Utility Model Publication No. 63-56003 (patent document 1)).

However, in the above-described cuff, the reliable wrapping may not necessarily be reproduced because the wrapping operation is left to the hand of the subject. If the reliable wrapping is not reproduced, variation occurs in the measurement value and it becomes difficult to accurately and stably measure the blood pressure information.

A cuff of various configurations has been proposed so that the cuff can be reliably wrapped around the site to be measured with satisfactory reproducibility. For instance, Japanese Unexamined Patent Publication No. 2002-209858 (patent document 2) discloses a cuff having a configuration in which a core material made from a curved elastic plate called a curler is interiorly accommodated in addition to the air bladder serving as the fluid bladder. In the cuff having such curler, the air bladder is pushed against the site to be measured with an appropriate pushing force and fixed by the curler after the attachment, and hence, the reliable fixation of the air bladder with respect to the site to be measured can be reproduced.

However, the cuff including the curler is configured by a member having rigidity of a certain extent, and thus, the handling becomes difficult with respect to pushing out the curler and placing it on the site to be measured when attaching the cuff.

In order to further facilitate the attachment in the cuff including the curler, Japanese Unexamined Patent Publication No. 2006-68318 (patent document 3) discloses a configuration of a cuff that enables attachment and detachment to the site to be measured with a one-touch operation. In the cuff disclosed in Japanese Unexamined Patent Publication No. 2006-68318, an elastic member such as a bias spring or a power transmission mechanism such as a slider is incorporated inside the cuff so that the cuff can be attached to the site to be measured with satisfactory reproducibility at an optimum tightening force by the biasing force of the bias spring and the radial size of the curler can be varied in cooperation with the operation of the user, whereby the cuff can be attached or detached with the one-touch operation.

Japanese Unexamined Patent Publication No. 2007-268052 (patent document 4) describes a configuration in which a second core for curving a first core by being attached on the outer side of the sheet-like first core (curler) in an overlapped manner is incorporated inside a cuff, and a fixing mechanism similar to a ratchet mechanism is arranged in the second core so that the diameter of the second core does not increase at the time of the tightening operation, and the radial size of the second core can be varied in cooperation with the operation of the user, whereby the attachment or detachment of the cuff can be enabled in a one-touch operation.

Furthermore, Japanese Unexamined Patent Publication No. 2007-75294 (patent document 5) and International Publication Pamphlet 03/101290 (patent document 6) disclose a cuff in which a winding device including a bias spring and a winding roller is incorporated inside the cuff, where one end of a band-shaped belt member attached with an air bladder is wound by the winding device so that the cuff is attached to the site to be measured with satisfactory reproducibility at an optimum tightening force by the biasing force of the bias spring.

Patent Document 1: Japanese Unexamined Utility Model Publication No. 63-56003
Patent Document 2: Japanese Unexamined Patent Publication No. 2002-209858
Patent Document 3: Japanese Unexamined Patent Publication No. 2006-68318
Patent Document 4: Japanese Unexamined Patent Publication No. 2007-268052
Patent Document 5: Japanese Unexamined Patent Publication No. 2007-75294
Patent Document 6: International Publication Pamphlet 03/101290

SUMMARY OF INVENTION

However, in the cuff disclosed in Japanese Unexamined Patent Publication No. 2007-75294 and International Publication Pamphlet 03/101290, the cuff has a non-annular form in a non-attached state, and hence, the cuff needs to be fixed to the site to be measured in a state annularly wrapped around the site to be measured and an engagement portion for engagement is arranged at one end and the other end of the band-shaped belt member. In the case of the cuff having this configuration, the operation of engaging the engagement portions while maintaining a state in which the band-shaped belt member is placed on the site to be measured is required in attachment, where the operation is to be carried out with both hands because the operation with one hand becomes difficult. Therefore, if the above-described configuration is adopted in a home sphygmomanometer in which the subject needs to wrap the cuff around one arm, the attachment of the cuff itself cannot be easily carried out alone.

In the cuff disclosed in Japanese Unexamined Patent Publication No. 2006-68318 and Japanese Unexamined Patent Publication No. 2007-268052, the cuff has an annular form in a non-attached state, and thus, the cuff can be attached and detached with a one-touch operation by one hand by inserting the site to be measured to a hollow opening, but the radial size of the cuff including the curler cannot be variably configured without limitation due to the device configuration, and the circumferential length of the site to the measured to which the cuff can be applied becomes limited, the device configuration becomes complex, and the manufacturing cost significantly increases.

Therefore, one or more embodiments of the present invention provides a cuff for a blood pressure information measurement device that has a simple configuration and can be inexpensively manufactured, and in which attachment with respect to the site to be measured can be easily carried out and the attachment with respect to the site to be measured can be stably reproduced, and a blood pressure information measurement device equipped with the same.

A cuff for a blood pressure information measurement device according to one or more embodiments of the present invention includes a fluid bladder, an exterior cover, and a fixing mechanism. The fluid bladder compresses a living body; the exterior cover has an annular portion to be wrapped around the living body and an overlapping portion to be overlapped on the annular portion, and is made from a band-shaped member that includes the fluid bladder. The fixing mechanism fixes the overlapping portion of the exterior cover to the annular portion of the exterior cover; and includes a roller rotatable only in one direction, a stopper facing the roller, and a pushing mechanism for pushing the stopper towards the roller. The overlapping portion of the exterior cover is inserted between the roller and the stopper, and the stopper is pushed towards the roller by the pushing mechanism so as to be pushed against the surface of the roller and fixed to the annular portion of the exterior cover by the friction force generated with the roller. The roller is rotatable only in a direction of reducing the size of the annular portion of the exterior cover when the overlapping portion of the exterior cover is sandwiched between the roller and the stopper.

In the cuff for the blood pressure information measurement device according to one or more embodiments of the present invention, the pushing mechanism is configured with a spring for biasing the stopper towards the roller.

In the cuff for the blood pressure information measurement device according to one or more embodiments of the present invention, the pushing mechanism may be configured by a member made from a shape memory alloy that contracts in a conduction state and extends in a non-conduction state.

The cuff for the blood pressure information measurement device according to one or more embodiments of the present invention further includes a release mechanism for releasing the fixing of the overlapping portion of the exterior cover to the annular portion of the exterior cover by separating the roller and the stopper.

In the cuff for the blood pressure information measurement device according to one or more embodiments of the present invention, the release mechanism is configured by a position adjustment mechanism for relatively and variably adjusting the position of the stopper with respect to the roller; in which case, the position adjustment mechanism includes a manually operable stopper position operating portion.

In the cuff for the blood pressure information measurement device according to one or more embodiments of the present invention, the release mechanism may be configured by a member made from a shape memory alloy that contracts in a conduction state and extends in a non-conduction state.

The cuff for the blood pressure information measurement device according to one or more embodiments of the present invention further includes a flexible curved elastic plate that is included in the exterior cover so as to be positioned along an outer side of the fluid bladder and that is elastically deformable along a radial direction of the annular portion of the exterior cover.

The cuff for the blood pressure information measurement device according to one or more embodiments of the present invention further includes a hook member, arranged at one end in a longitudinal direction of the exterior cover, for maintaining the exterior cover in an annular form by being inserted with the other end in the longitudinal direction of the exterior cover and enabling a portion closer to the other end of the exterior cover to be folded back along a circumferential direction of the annular portion of the exterior cover; in which case the overlapping portion of the exterior cover is configured by the exterior cover of the portion folded back using the hook member.

In the cuff for the blood pressure information measurement device according to one or more embodiments of the present invention, the surface of the roller has an irregularity.

In the cuff for the blood pressure information measurement device according to one or more embodiments of the present invention, the surface of the roller is covered with a rubber material.

In the cuff for the blood pressure information measurement device according to one or more embodiments of the present invention, a pull tab is arranged at the other end of the exterior cover.

A blood pressure information measurement device according to one or more embodiments of the present invention includes a cuff for a blood pressure information measurement device described above, an expansion/contraction mechanism for expanding and contracting the fluid bladder; and a blood pressure information acquiring unit for acquiring blood pressure information.

One or more embodiments of the present invention include a cuff for a blood pressure information measurement device that has a simple configuration, is inexpensively manufactured, and easily carries out and stably reproduces attachment with respect to the site to be measured, and a blood pressure information measurement device equipped with the same.

BRIEF DESCRIPTION OF THE DRAWINGS

FIG. 3 is a flowchart showing the flow of processes of the sphygmomanometer according to the first embodiment of the present invention.

FIG. 4 is a cross-sectional view showing a detailed structure of a cuff for a sphygmomanometer according to the first embodiment of the present invention.

DETAILED DESCRIPTION OF INVENTION

Embodiments of the present invention will be described in detail with reference to the drawings. In the embodiments described below, description will be made by illustrating a cuff for a sphygmomanometer intended to be used by being wrapped around the upper arm and a sphygmomanometer capable of measuring the blood pressure value such as the systolic blood pressure value and the diastolic blood pressure value using the same, as the cuff for the blood pressure information measurement device, and the blood pressure information measurement device equipped with the same.

First Embodiment

Figure 1:
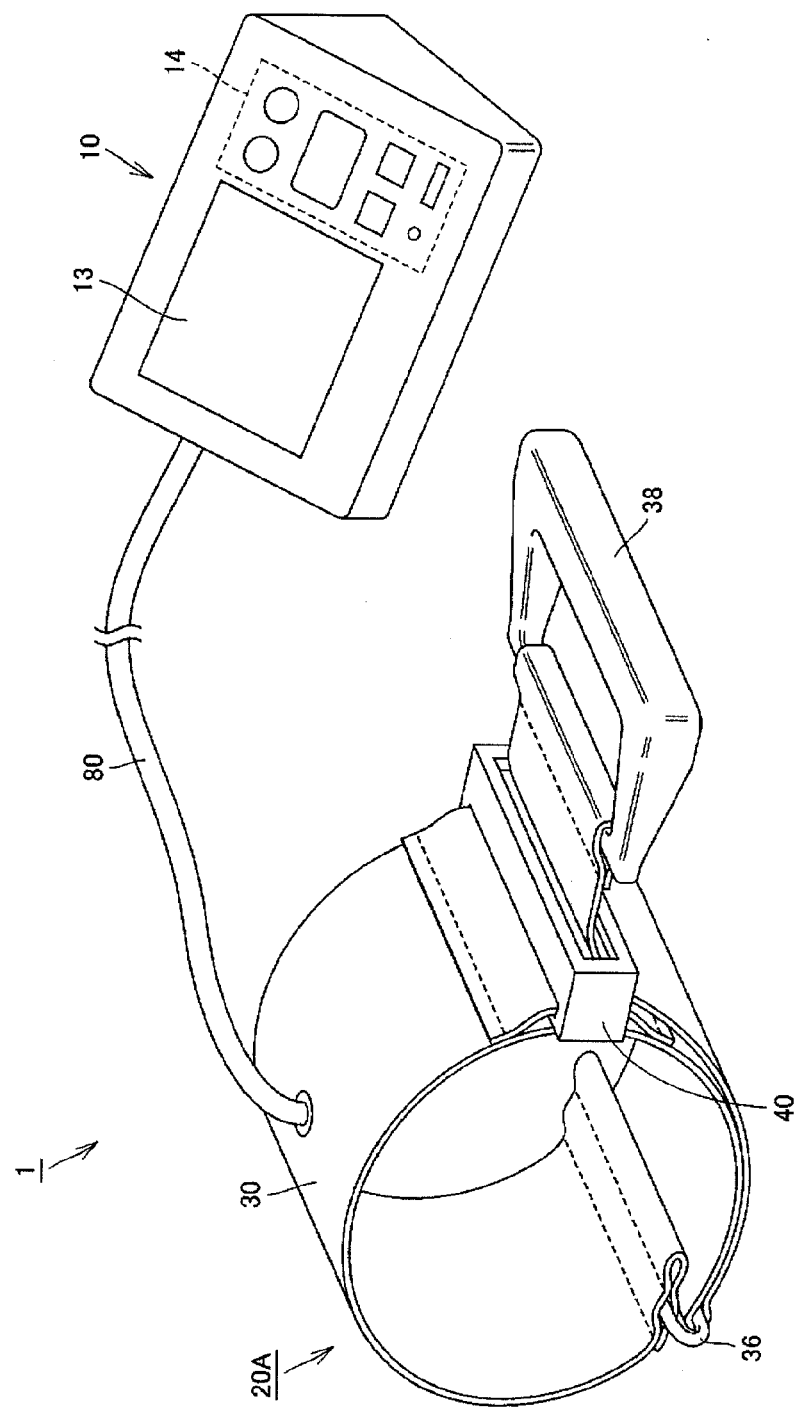
FIG. 1 is a perspective view showing an outer appearance structure of a cuff for a sphygmomanometer and a sphygmomanometer equipped with the same according to a first embodiment of the present invention.
Figure 2:
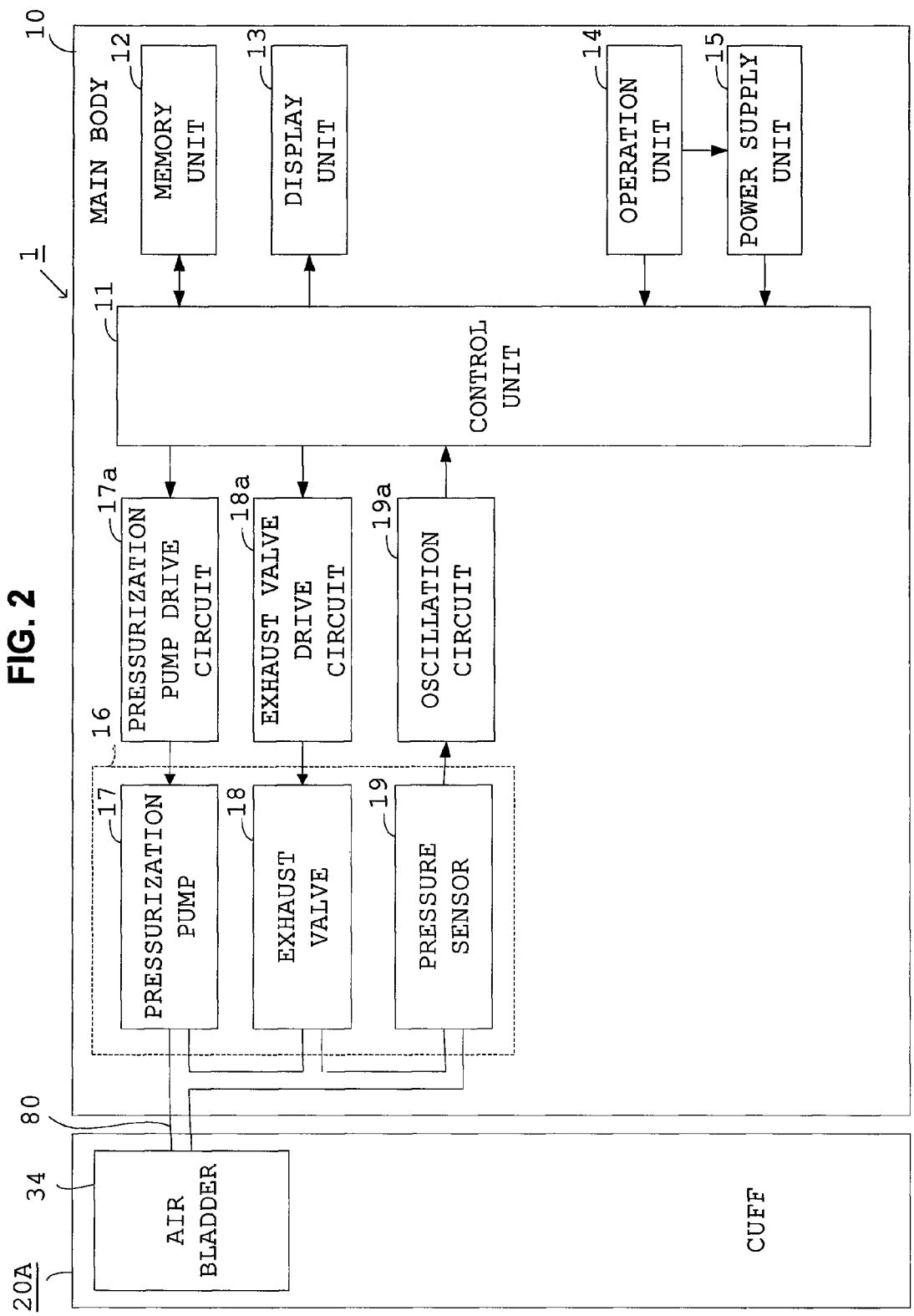
FIG. 2 is a view showing the configuration of functional blocks of the sphygmomanometer according to the first embodiment of the present invention.

FIG. 1 is a perspective view showing an outer appearance structure of a sphygmomanometer according to a first embodiment of the present invention, and FIG. 2 is a view showing the configuration of functional blocks of the sphygmomanometer according to the present embodiment. First, the outer appearance structure and the configuration of the functional blocks of the sphygmomanometer according to the present embodiment will be described with reference to FIG. 1 and FIG. 2.

As shown in FIG. 1, a sphygmomanometer 1 according to the present embodiment includes a main body 10, a cuff 20A, and an air tube 80. The main body 10 has a box-shaped housing, where a display unit 13 and an operation unit 14 are arranged on the upper surface thereof. The main body 10 is used by being mounted on a mounting surface of a table or the like at the time of the measurement. The cuff 20A mainly includes an exterior cover 30, and an air bladder 34 (see FIG. 2, FIG. 4, etc.), and has an annular portion to which the upper arm can be inserted from the axial direction. The cuff 20A is used by being attached to the upper arm at the time of the measurement. The air tube 80 connects the main body 10 and the cuff 20A, which are separately configured.

As shown in FIG. 2, the main body 10 includes a control unit 11, a memory unit 12, a power supply unit 15, a pressurization pump 17, an exhaust valve 18, a pressure sensor 19, a pressurization pump drive circuit 17a, an exhaust valve drive circuit 18a, and an oscillation circuit 19a, in addition to the display unit 13 and the operation unit 14. The pressurization pump 17, the exhaust valve 18, and the pressure sensor 19 correspond to an air system component 16 arranged in the sphygmomanometer 1, and in particular, the pressurization pump 17 and the exhaust valve 18 correspond to an expansion/contraction mechanism for expanding and contracting the air bladder 34.

The air bladder 34 is a fluid bladder for compressing the upper arm in the attached state, and interiorly includes an expansion/contraction space serving as an inner cavity. The air bladder 34 is connected to the pressurization pump 17, the exhaust valve 18, and the pressure sensor 19, which are the air system component 16, through the air tube 80.

The control unit 11 is configured by, for example, a CPU (Central Processing Unit), and is a site that controls the entire sphygmomanometer 1. The memory unit 12 is configured by, for example, a ROM (Read Only Memory) or a RAM (Random Access Memory), and is a site that stores programs for causing the control unit 11 and the like to execute the processing procedure for the blood pressure value measurement, and stores the measurement results and the like. The display unit 13 is configured by, for example, an LCD (Liquid Crystal Display), and is a site that displays the measurement results and the like. The operation unit 14 is a site that inputs a command from the outside to the control unit 11 and the power supply unit 15 when receiving an operation by a subject or the like. The power supply unit 15 is a site that supplies power serving as a power supply to the control unit 11.

The control unit 11 inputs a control signal for driving the pressurization pump 17 and the exhaust valve 18 to the pressurization pump drive circuit 17a and the exhaust valve drive circuit 18a, and also inputs the blood pressure value serving as a measurement result to the memory unit 12 and the display unit 13. The control unit 11 also includes a blood pressure information acquiring section (not shown) for acquiring the blood pressure value of the subject based on the pressure value detected by the pressure sensor 19, where the blood pressure value acquired by the blood pressure information acquiring section is input to the memory unit 12 and the display unit 13 as the measurement result. The sphygmomanometer 1 may separately include an output unit for outputting the blood pressure value serving as the measurement value to an external device (e.g., PC (Personal Computer), printer, etc.). For example, the serial communication line, the write device to various types of recording media, and the like can be used for the output unit.

The pressurization pump drive circuit 17a controls the operation of the pressurization pump 17 based on the control signal input from the control unit 11. The exhaust valve drive circuit 18a controls the opening and closing operation of the exhaust valve 18 based on the control signal input from the control unit 11. The pressurization pump 17 pressurizes the pressure (hereinafter also referred to as "cuff pressure") inside the air bladder 34 by supplying air to the inner cavity of the air bladder 34, the operation of which being controlled by the pressurization pump drive circuit 17a. The exhaust valve 18 maintains the pressure inside the air bladder 34 or depressurizes the cuff pressure by opening the inner cavity of the air bladder 34 to the outside, the operation of which being controlled by the exhaust valve drive circuit 18a. The pressure sensor 19 inputs an output signal corresponding to the pressure inside the air bladder 34 to the oscillation circuit 19a. The oscillation circuit 19a generates a signal having an oscillating frequency corresponding to the signal input from the pressure sensor 19, and inputs the generated signal to the control unit 11.

FIG. 3 is a flowchart showing the flow of processes of the sphygmomanometer according to the present embodiment. The flow of processes of the sphygmomanometer according to the present embodiment will now be described with reference to FIG. 3. The program according to the flowchart is stored in advance in the memory unit 12, where the processes are executed when the control unit 11 reads out the program from the memory unit 12 and executes the same.

When measuring the blood pressure value, the subject attaches the cuff 20A to the upper arm in advance, and operates the operation unit 14 arranged on the main body 10 in this state to turn ON the power of the sphygmomanometer 1. The power serving as the power supply is thereby supplied from the power supply unit 15 to the control unit 11 thus driving the control unit 11. As shown in FIG. 3, the control unit 11 first carries out initialization of the sphygmomanometer 1 after being driven (step S101).

The control unit 11 then waits for an instruction to start the measurement from the subject, where when the instruction to start the measurement is made from the subject by operating the operation unit 14, the control unit 11 closes the exhaust valve 18 and starts the drive of the pressurization pump 17 to raise the cuff pressure of the air bladder 34 (step S102). When the cuff pressure reaches a predetermined level for measuring the blood pressure value in the process of pressurizing the air bladder 34, the control unit 11 stops the pressurization pump 17, gradually opens the closed exhaust valve 18 to gradually exhaust the air in the air bladder 34, and gradually depressurizes the cuff pressure (step S103). In the sphygmomanometer 1 according to the present embodiment, the blood pressure value is measured in the micro-speed depressurization process of the cuff pressure.

The control unit 11 then calculates the blood pressure value such as the systolic blood pressure value and the diastolic blood pressure value through a known procedure (step S104). Specifically, the control unit 11 extracts the pulse wave information based on the oscillating frequency obtained from the oscillating circuit 19a in the process of gradually depressurizing the cuff pressure of the air bladder 34. The control unit 11 then calculates the blood pressure value based on the extracted pulse wave information. After the blood pressure value is calculated in step S104, the control unit 11 displays the blood pressure value serving as the measurement result on the display unit 13 (step S105) and stores the relevant blood pressure value in the memory unit 12.

Thereafter, the control unit 11 completely exhausts the air in the air bladder 34 by opening the air bladder 34 (step S106), and waits for a command to turn OFF the power of the subject to terminate the operation. The measurement method described above is based on a so-called depressurization measurement method for detecting the pulse wave at the time of depressurization of the air bladder 34, but a so-called pressurization measurement method for detecting the pulse wave at the time of pressurization of the air bladder 34 may of course be adopted.

Figure 5A:
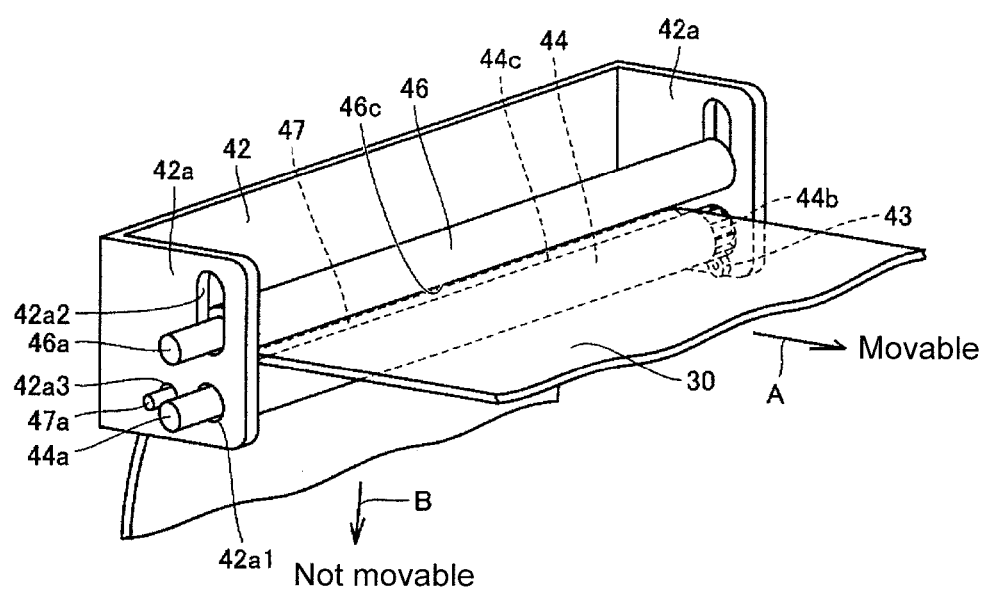
FIG. 5A is a schematic perspective view describing the configuration and the operation of a fixing mechanism arranged in the cuff for the sphygmomanometer according to the first embodiment of the present invention.
Figure 5B:
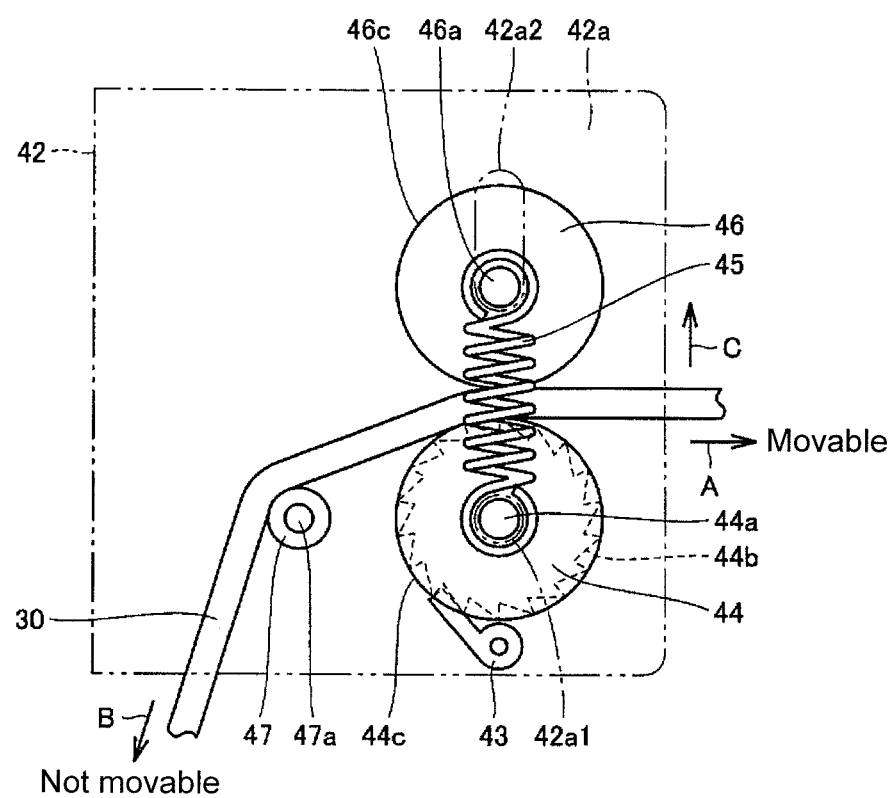
FIG. 5B is a schematic side view describing the configuration and the operation of the fixing mechanism arranged in the cuff for the sphygmomanometer according to the first embodiment of the present invention.
Figure 6A:
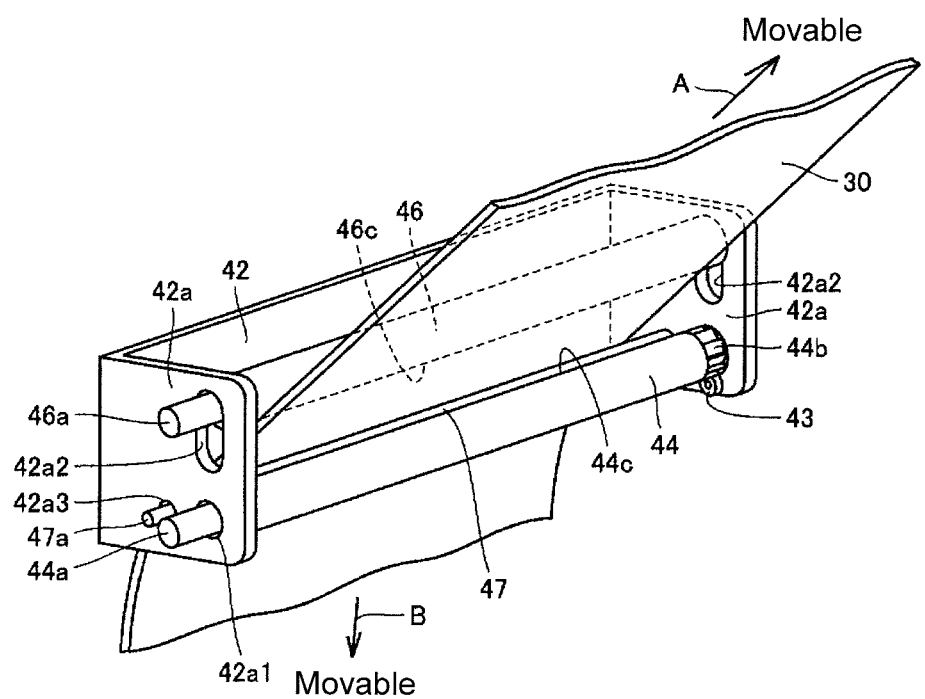
FIG. 6A is a schematic perspective view describing the configuration and the operation of the fixing mechanism arranged in the cuff for the sphygmomanometer according to the first embodiment of the present invention.
Figure 6B:
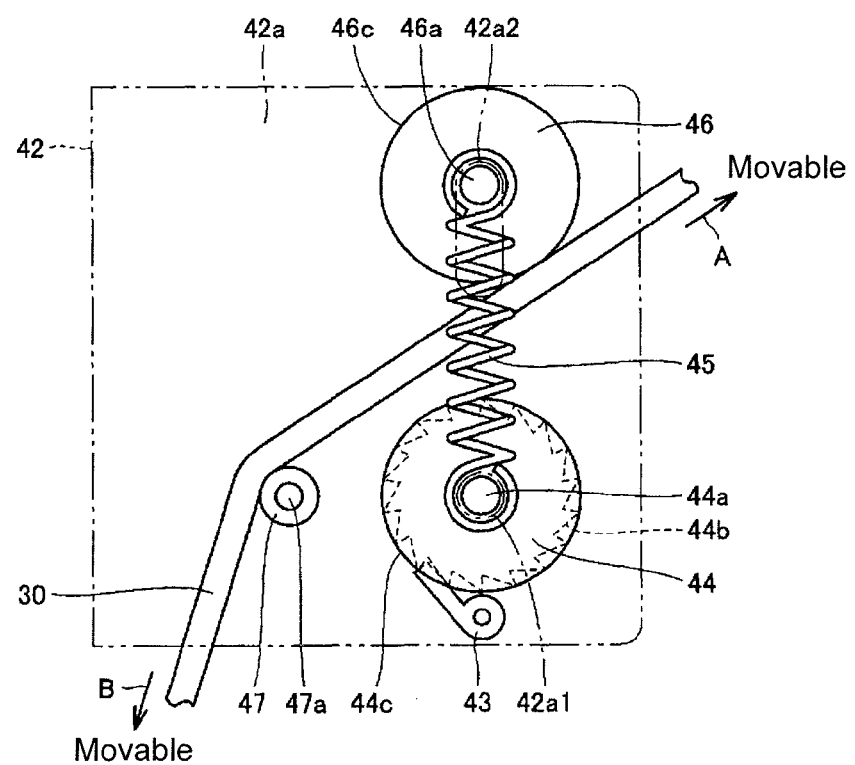
FIG. 6B is a schematic side view describing the configuration and the operation of the fixing mechanism arranged in the cuff for the sphygmomanometer according to the first embodiment of the present invention.

FIG. 4 is a cross-sectional view showing a detailed structure of a cuff for a sphygmomanometer according to the present embodiment, and FIG. 5A, FIG. 5B, FIG. 6A, and FIG. 6B are views describing the configuration and the operation of a fixing mechanism arranged in the cuff for the sphygmomanometer. FIG. 5A and FIG. 5B are a schematic perspective view and a schematic side view showing a state in which the exterior cover is fixed by the fixing mechanism, and FIG. 6A and FIG. 6B are a schematic perspective view and a schematic side view showing a state in which the fixation of the exterior cover by the fixing mechanism is released. The detailed structure and the operation of the cuff for the sphygmomanometer according to the present embodiment will now be described with reference to the drawings.

As shown in FIG. 4, the cuff 20A according to the present embodiment mainly includes the air bladder 34, the exterior cover 30, an annular ring 36 serving as a hooking member, a pull tab 38, and a fixing unit 40 serving as a fixing mechanism.

The air bladder 34 is made from a bag-shaped member suitably formed using a resin sheet, and interiorly includes an expanding and contracting space. The air bladder 34 that is formed by overlapping two resin sheets and welding the circumferential edge to be formed into a bag shape is used, for example. The expanding and contracting space of the air bladder 34 is connected to the pressurization pump 17 and the exhaust valve 18 through the air tube 80, where pressurization and depressurization are carried out by the pressurization pump 17 and the exhaust valve 18. The material of the resin sheet configuring the air bladder 34 may be any material as long as it excels in stretchability and air does not leak out from the expanding and contracting space after welding. From such standpoint, the suitable material of the resin sheet is ethylene vinyl acetate copolymer (EVA), flexible polyvinyl chloride (PVC), polyurethane (PU), natural rubber (NR), or the like.

The exterior cover 30 is formed as a bag-shaped band member by overlapping an inner side cover 31, which is to be brought into contact with the surface of the upper arm in the attached state, and an outer side cover 32, which is to be positioned on the outer side than the inner side cover 31 in the attached state, and joining (e.g., sewing, welding, etc.) the circumferential edges thereof, and includes one end 30a and the other end 30b in the longitudinal direction. The exterior cover 30 includes the air bladder 34. A member sufficiently excelling in stretchability is suitably used for the inner side cover 31 of the exterior cover 30 so that the compression force applied on the upper arm by the expansion of the air bladder 34 is not inhibited by the inner side cover 31. On the other hand, a member having poor stretchability compared to the inner side cover 31 is used for the outer side cover 32. From such a standpoint, cloth made from a synthetic fiber including polyamide (PA) and polyester in which the magnitude of stretchability can be relatively easily adjusted is used for the exterior cover 30.

The annular ring 36 is attached to one end 30a of the exterior cover 30. More specifically, the portion closer to one end 30a of the exterior cover 30 is inserted to the annular ring 36 and then folded back and sewed, so that the annular ring 36 is attached to one end 30a of the exterior cover 30. The annular ring 36 is configured by, for example, a metal member in which friction is less likely to occur with the exterior cover 30, and includes an insertion hole to which the portion closer to the other end 30b of the exterior cover 30 can be inserted.

The pull tab 38 is attached to the other end 30b of the exterior cover 30. More specifically, the portion closer to the other end 30b of the exterior cover 30 is inserted to the pull tab 38 and then folded back and sewed, so that the pull tab 38 is attached to the other end 30b of the exterior cover 30. The pull tab 38 is formed by, for example, injection molding with a resin material as the raw material, and includes a grip that can be gripped with hand.

As shown in FIG. 4, FIG. 5A, FIG. 5B, FIG. 6A, and FIG. 6B, the fixing unit 40 is arranged at a predetermined position on the outer surface of the exterior cover 30. The fixing unit 40 mainly includes a housing 41 fixed to the exterior cover 30, a supporting frame 42 arranged inside the housing 41, a roller 44 supported by the supporting frame 42, a stopper 46 and a drive roller 47, and a coil spring 45 serving as a pushing mechanism assembled to the roller 44 and the stopper 46.

The housing 41 is made from a box-shaped member extending along the axial direction of the cuff 20A, and includes openings 41a, 41b to which the portion closer to the other end 30b of the exterior cover 30 is inserted. The supporting frame 42 is formed by, for example, press working both ends of a metal flat plate member and is fixed to the housing 41 while being accommodated inside the housing 41. The supporting frame 42 includes a pair of side walls 42a at both ends in the longitudinal direction (direction along axial direction of cuff 20A).

The roller 44 is arranged inside the housing 41 so as to extend along the axial direction of the cuff 20A, and is rotatably supported by the pair of side walls 42a of the supporting frame 42. More specifically, each of the pair of side walls 42a of the supporting frame 42 includes a shaft supporting hole 42a1 having a perfect circle shape, where a shaft 44a of the roller 44 is inserted to the shaft supporting hole 42a1 so that the roller 44 is rotatably supported with the supporting frame 42.

A clutch plate 44b is arranged at a predetermined position in the vicinity of both ends of the roller 44, respectively, where each clutch plate 44b is fixed to the shaft 44a of the roller 44. The clutch plate 44b is made from a disc-shaped member, and wedge-shaped teeth are continuously arranged along the circumferential direction on the outer circumferential surface thereof. A clutch nail 43 is arranged at a predetermined position of the pair of side walls 42a of the supporting frame 42, respectively, and each clutch nail 43 gears with the tooth of the clutch plate 44b. The clutch plate 44b and the clutch nail 43 function as a so-called one-way clutch, where the roller 44 can rotate only in a predetermined direction when the clutch nail 43 gears with the clutch plate 44b.

According to one or more embodiments of the present invention, a surface 44c of the roller 44 is covered with a rubber material. According to one or more embodiments of the present invention, the material of the rubber material generates a large friction force with the exterior cover 30 in a state of being pushed by the exterior cover 30, and rubber such as styrene butadiene rubber (SBR) or butadiene rubber (BR), ethylene propylenediene rubber (EPDM), chloroprene rubber (CR), acrylonitrile butadiene rubber (NBR), thermoplastic elastomer (TPE), urethane rubber (U), and silicone rubber (Q) can be suitably used.

The stopper 46 is arranged in the housing 41 so as to extend along the axial direction of the cuff 20A, and is movably and rotatably supported by the pair of side walls 42a of the supporting frame 42. More specifically, each of the pair of side walls 42a of the supporting frame 42 has an oval shaft supporting hole 42a2, where a shaft 46a of the stopper 46 is inserted to the shaft supporting hole 42a2 so that the roller 44 is movably and rotatably supported by the supporting frame 42. According to one or more embodiments of the present invention, the stopper 46 in which the surface 46c is covered with a rubber material similar to the roller 44 described above is used, but is not limited thereto, and it may be configured by a member made of metal or resin.

The shaft supporting hole 42a2 is configured so that the stopper 46 is movable between a position proximate to the roller 44 and a position distant from the roller 44, so that the stopper 46 can take a state (state shown in FIG. 5A and FIG. 5B) of being arranged at a position proximate to the roller 44, and a state (state shown in FIG. 6A and FIG. 6B) of being arranged at a position distant from the roller 44.

The driven roller 47 is arranged in the housing 41 so as to extend along the axial direction of the cuff 20A, and is rotatably supported by the pair of side walls 42a of the supporting frame 42. More specifically, each of the pair of side walls 42a of the supporting frame 42 includes a shaft supporting hole 42a3 having a perfect circle shape, where a shaft 47a of the driven roller 47 is inserted to the shaft supporting hole 42a3 so that the driven roller 47 is rotatably supported with the supporting frame 42. According to one or more embodiments of the present invention, the driven roller 47 having a smooth surface is used, but may be configured by, for example, a member made of metal or resin.

As shown in FIG. 5B and FIG. 6B, the roller 44 and the stopper 46 are assembled with a coil spring 45 (not shown in FIG. 5A and FIG. 6A). The coil spring 45 biases the stopper 46 towards the roller 44, where one end is fixed to the shaft 44a of the roller 44 and the other end is fixed to the shaft 46a of the stopper 46. The stopper 46 thus takes a state (i.e., state shown in FIG. 5A and FIG. 5B) of being arranged at the position proximate to the roller 44 of the two states described above with no external force being applied.

As shown in FIG. 4, in the cuff 20A according to the present embodiment, the other end 30b of the exterior cover 30 is maintained in an annular form by being inserted to the insertion hole of the annular ring 36 attached to the one end 30a of the exterior cover 30, and the portion closer to the other end 30b of the exterior cover 30 is folded back with the annular ring 36 as the base point along the circumferential direction of the annular portion of the exterior cover 30 and then overlapped on the annular portion. Therefore, the portion closer to the other end 30b of the exterior cover 30 folded back with the annular ring 36 as the base point and overlapped on the annular portion corresponds to the overlapping portion. The portion closer to the other end 30b of the exterior cover 30 that is folded back is pulled out to the outside of the fixing unit 40 through the fixing unit 40 attached to the annular portion of the exterior cover 30. The pull tab 38 is attached to the distal end of the exterior cover 30 at the portion pulled out from the fixing unit 40.

The folded back portion (i.e., overlapping portion) of the exterior cover 30 is inserted to the openings 41a, 41b formed in the housing 41 of the fixing unit 40, and is brought into contact with the driven roller 47 at inside the housing 41 of the fixing unit 40 and is also inserted between the roller 44 and the stopper 46.

As shown in FIG. 5A and FIG. 5B, in the state in which the stopper 46 is arranged at a position proximate to the roller 44, the folded back portion of the exterior cover 30 is pushed against the roller 44 by the stopper 46 so that a large friction force is generated between the surface of the exterior cover 30 and the surface 44c of the roller 44, and the folded back portion of the exterior cover 30 is fixed to the annular portion of the exterior cover 30 through the fixing unit 40. As the rotation direction of the roller 44 is regulated when the clutch plate 44b and the clutch nail 43 gear with each other, the folded back portion of the exterior cover 30 can move in the direction of the arrow A in the figure but cannot move in the direction of the arrow B in the figure. Thus, the operation can be carried out such that the size of the annular portion of the cuff 20A becomes smaller, but the operation cannot be carried out such that the size of the annular portion of the cuff 20A becomes larger.

On the other hand, as shown in FIG. 6A and FIG. 6B, in the state in which the stopper 46 is arranged at a position distant from the roller 44, the folded back portion of the exterior cover 30 is not pushed against the roller 44 by the stopper 46, and the folded back portion of the exterior cover 30 is not fixed to the annular portion. Therefore, the folded back portion of the exterior cover 30 can move not only in the direction of the arrow A in the figure, but also in the direction of the arrow B in the figure. Thus, the operation can be carried out such that the size of the annular portion of the cuff 20A becomes smaller and larger.

In order to obtain the state shown in FIG. 6A and FIG. 6B, the portion closer to the other end 30b of the exterior cover 30 is to be pulled up in the direction of the arrow C shown in FIG. 6A and FIG. 6B using the pull tab 38 such that the folded back portion of the exterior cover 30 moves away from the roller 44 against the biasing force of the coil spring 45 in the state shown in FIG. 5A and FIG. 5B, where the operation towards the upper side of the pull tab 38 is to be stopped when returning the state to the state shown in FIG. 5A and FIG. 5B.

In the cuff 20A described above, the attachment to the upper arm is carried out according to the following attachment procedure. First, one hand is inserted to the annular portion of the cuff 20A from the axial direction, and the annular portion of the cuff 20A is placed on the upper arm of the inserted arm. The pull tab 38 of the cuff 20A is then gripped and pulled with the other hand so that the diameter of the annular portion of the cuff 20A is reduced, thus obtaining an appropriate fitting to the upper arm without a gap. In this case, the diameter of the annular portion of the cuff 20A does not increase and become loose even if the force of pulling the pull tab 38 is loosened due to the action of the one way clutch including the clutch plate 44b and the clutch nail 43. The attachment of the cuff 20A to the upper arm is thereby completed.

Meanwhile, when detaching the cuff 20A from the upper arm, the pull tab 38 is gripped and the portion closer to the other end 30b of the exterior cover 30 is pulled up to the upper side so that a gap is formed between the upper arm and the annular portion of the cuff 20A, and the upper arm is removed from the annular portion of the cuff 20A thus completing the detachment.

In the description made above, the cuff 20A can be attached to the upper arm with a very simple operation of operating the pull tab 38 according to the cuff 20A for the sphygmomanometer and the sphygmomanometer 1 equipped with the same according to the present embodiment. The diameter of the annular portion of the cuff 20A does not increase to loosen the cuff 20A unless a special operation is carried out, and hence, the cuff 20A can be very easily attached to the upper arm. Therefore, the fitted attachment of the cuff 20A to the upper arm can be facilitated by adopting the configuration described above, and the cuff can be attached to the upper arm stably and with satisfactory reproducibility.

In the cuff 20A for the sphygmomanometer and the sphygmomanometer 1 equipped with the same according to the present embodiment, the fixing mechanism for maintaining the tightening state of the cuff with a simple configuration using the roller 44 and the stopper 46 biased towards the roller 44 is configured. Therefore, the cuff that has satisfactory reproducibility and that can be stably attached can be manufactured without adopting a fixing mechanism of a complex configuration, and the cuff can be manufactured at very low cost.

As the cuff can be attached with a simple operation, the cuff 20A can be easily attached even by the elderly and women having relatively weak power, and hence, the cuff for the sphygmomanometer and the sphygmomanometer equipped with the same that excel greatly in handling are obtained. Furthermore, because the attachment can be easily carried out, the annular portion of the cuff 20A can be relatively easily positioned and attached to an appropriate position of the upper arm, whereby occurrence of measurement error due to a shift in the attachment position can be reduced, and the measurement of an accurate blood pressure value can be carried out. The cuff that can be applied to any subject including subjects with long circumferential length of the upper arm and subjects with short circumferential length of the upper arm by making the length of the exterior cover 30 sufficiently long, and the sphygmomanometer equipped with the same can be obtained.

Therefore, according to the cuff 20A for the sphygmomanometer and the sphygmomanometer 1 equipped with the same according to the present embodiment, there are obtained the cuff for the sphygmomanometer and the sphygmomanometer equipped with the same that have a simple configuration and can be inexpensively manufactured, and in which attachment with respect to the upper arm serving as the site to be measured can be easily carried out, and the attachment with respect to the upper arm can be stably reproduced.

Figure 7A:
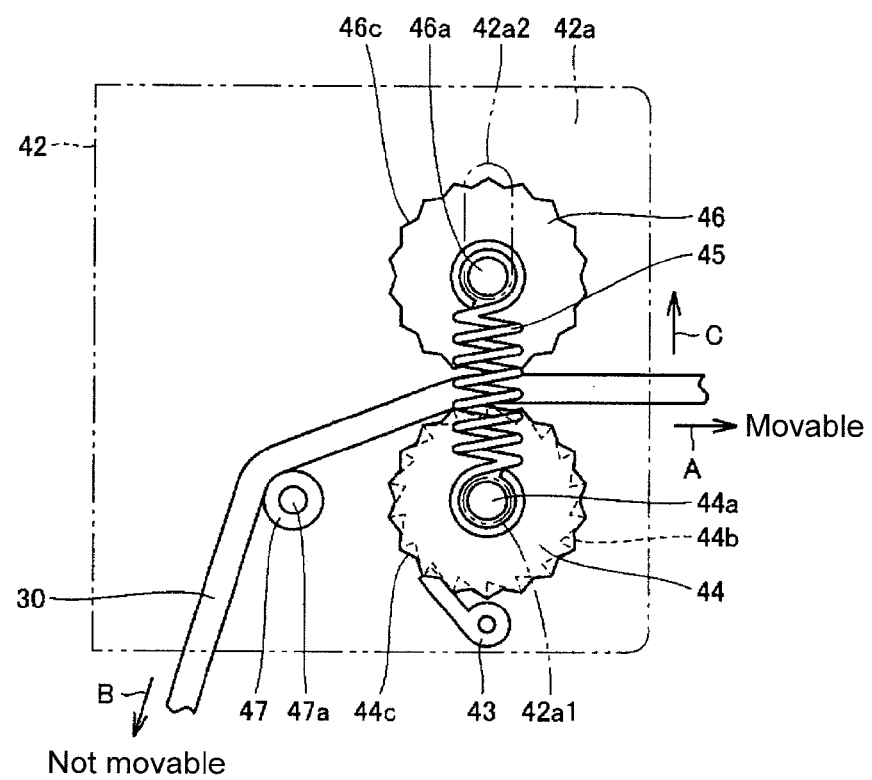
FIG. 7A is a schematic side view describing the configuration and the operation of the fixing mechanism of the cuff for the sphygmomanometer according to a first variant.
Figure 7B:
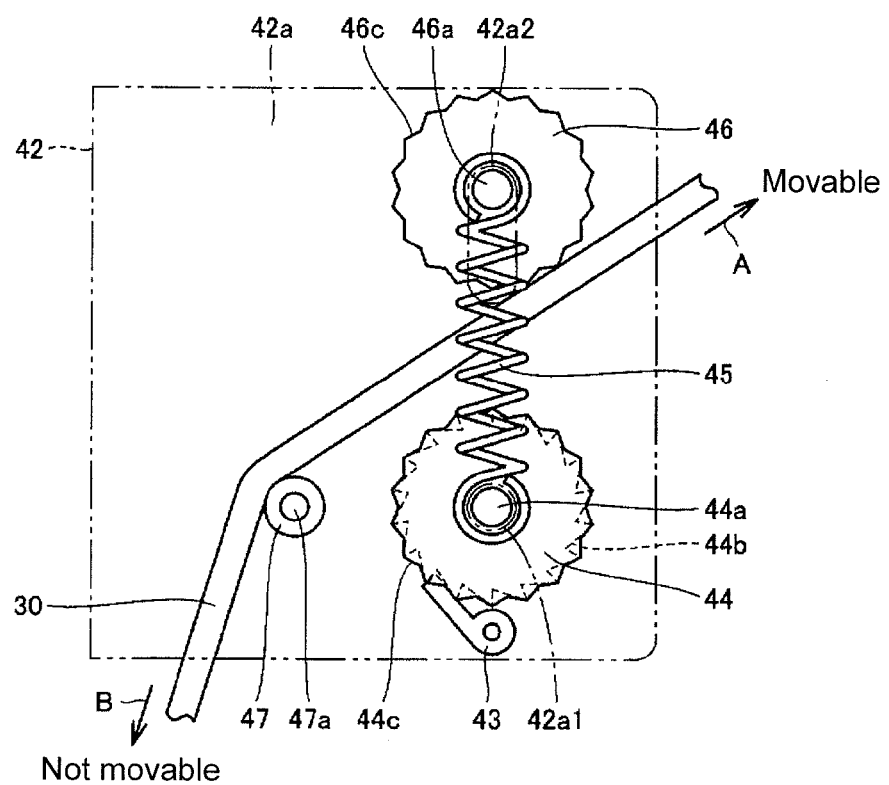
FIG. 7B is a schematic side view describing the configuration and the operation of the fixing mechanism of the cuff for the sphygmomanometer according to the first variant.
Figure 8A:
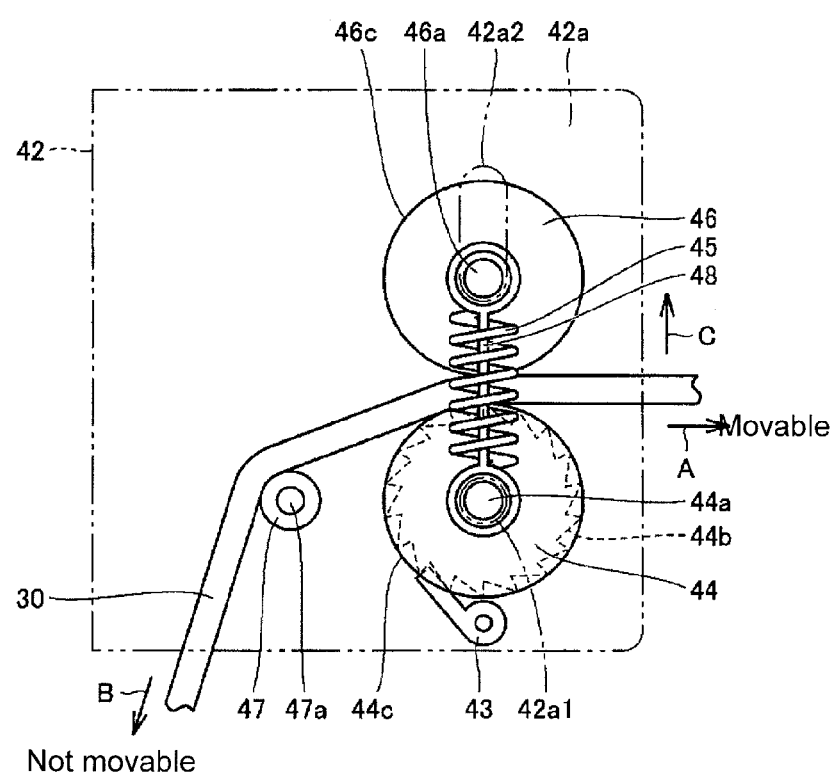
FIG. 8A is a schematic side view describing the configuration and the operation of the fixing mechanism of the cuff for the sphygmomanometer according to a second variant.
Figure 8B:
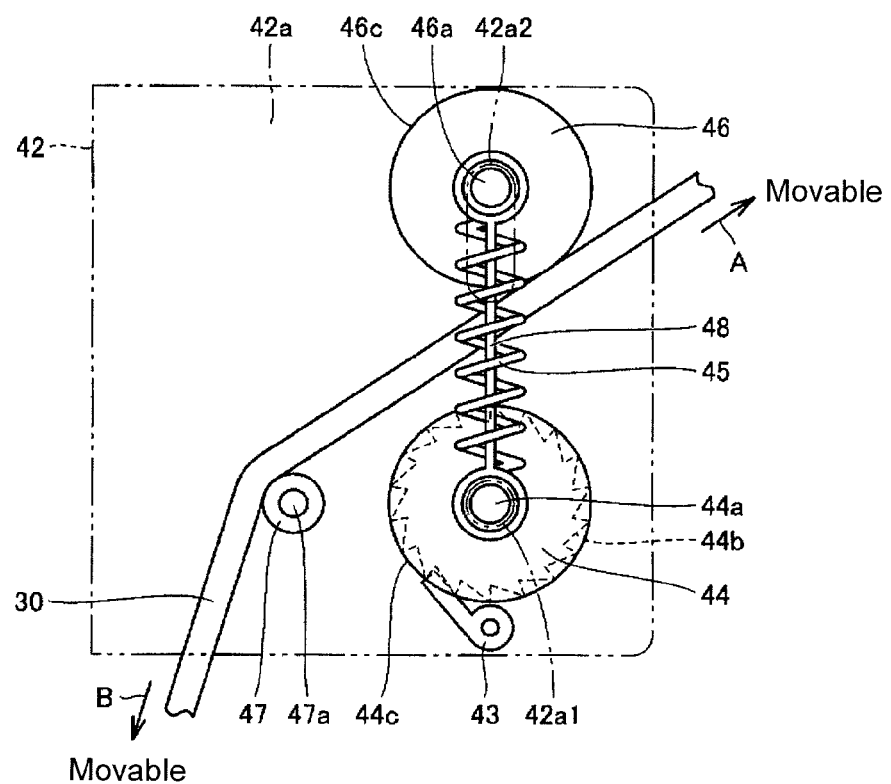
FIG. 8B is a schematic side view describing the configuration and the operation of the fixing mechanism of the cuff for the sphygmomanometer according to the second variant.

FIG. 7A, FIG. 7B, FIG. 8A, and FIG. 8B are views showing the configuration and the operation of the fixing mechanism of the cuff for the sphygmomanometer according to first and second variants of the present embodiment, where FIG. 7A and FIG. 8A are schematic side views showing a state in which the exterior cover is fixed by the fixing mechanism, and FIG. 7B and FIG. 8B are schematic side views showing a state in which the fixation by the fixing mechanism of the exterior cover is released. The cuff for the sphygmomanometer and the sphygmomanometer according to the first and second variants have configurations similar to the cuff for the sphygmomanometer and the sphygmomanometer in the present embodiment described above other than the aspect described below, and hence, the description thereof will not be repeated.

As shown in FIG. 7A and FIG. 7B, the cuff for the sphygmomanometer according to the first variant has irregularities formed on the surfaces 44c, 46c of the roller 44 and the stopper 46. The irregularities formed on the surfaces 44c, 46c of the roller 44 and the stopper 46 may be plural grooves extending along the axial direction of the cuff, or may be irregularities evenly arranged over the entire surface when the surfaces 44c, 46c are seen in plan view. According to one or more embodiments of the present invention, the surface 44c of the roller 44 and the surface 46c of the stopper 46 are covered with a rubber material similar to the case of the cuff for the sphygmomanometer according to the present embodiment described above, but may also be covered with a member other than the rubber material.

The irregularities are provided to enhance the friction force between the exterior cover 30, which is inserted between the roller 44 and the stopper 46, and the surfaces 44c, 46c of the roller 44 and the stopper 46 formed with the irregularities, where the irregularities may be provided only on either one of the surfaces of the roller 44 and the stopper 46. With such configuration, the exterior cover 30 can be more reliably fixed, and hence, the cuff 20A can be more reliably attached in a fitted manner to the upper arm.

As shown in FIG. 8A and FIG. 8B, the cuff for the sphygmomanometer according to the second variant has a pushing member 48 serving as a pushing mechanism assembled to the roller 44 and the stopper 46. The pushing member 48 is made from a shape memory alloy (SMA) that contracts in the conduction state so that the longitudinal length is reduced and extends in the non-conduction state so that the longitudinal length increases. The roller 44 and the stopper 46 are assembled with a coil spring 45 for biasing in a direction of widening a gap between the roller 44 and the stopper 46.

Specifically, the pushing member 48 made of a shape memory alloy has one end in the longitudinal direction fixed to the shaft 44a of the roller 44 and the other end in the longitudinal direction fixed to the shaft 46a of the stopper 46. Thus, in the conduction state in which the current is applied to the pushing member 48, the pushing member 48 contracts against the biasing force of the coil spring 45 as shown in FIG. 8A so that the stopper 46 moves closer to the roller 44 and the exterior cover 30 is pushed against the roller 44, and in the non-conduction state in which the current is not applied to the pushing member 48, the pushing member 48 extends in accordance with the biasing force of the coil spring 45 as shown in FIG. 8B so that the stopper 46 moves away from the roller 44, and thus, the exterior cover 30 is not pushed against the roller 44.

Therefore, according to the configuration described above, whether the folded back portion of the exterior cover 30 is fixed or not fixed to the annular portion of the cover 30 can be electrically controlled by switching the conduction/non-conduction state with respect to the pushing member 48. Therefore, the fixing state of the cuff can be easily switched, and furthermore, the cuff can be attached with satisfactory operability by arranging a switch or the like for switching the conduction/non-conduction state with respect to the pushing member 48 in either the cuff or the main body. The switch for switching the conduction/non-conduction state with respect to the pushing member 48 may be made common with a power supply button for switching ON/OFF of the power of the main body. The coil spring 45 supplementary supports the operation of the pushing member 48, where a configuration of arranging only the pushing member 48 without arranging the coil spring 45 may be adopted in some cases.

In the configuration shown in FIG. 8A and FIG. 8B, if the coil spring 45 assembled to the roller 44 and the stopper 46 is changed to a coil spring for biasing in a direction of reducing the gap between the roller 44 and the stopper 46, the member made of the shape memory alloy can also be used as a release mechanism (release member 48) for releasing the fixation of the exterior cover 30. In this case, in the conduction state in which the current is applied to the release member 48, the release member 48 contracts in accordance with the biasing force of the coil spring 45 as shown in FIG. 8A so that the stopper 46 moves closer to the roller 44 and the exterior cover 30 is pushed against the roller 44, and in the non-conduction state in which the current is not applied to the release member 48, the release member 48 extends against the biasing force of the coil spring 45 as shown in FIG. 8B so that the stopper 46 moves away from the roller 44 and the exterior cover 30 is not pushed against the roller 44. Effects similar to the above effects can also be obtained with such configuration.

Second Embodiment

Figure 9:
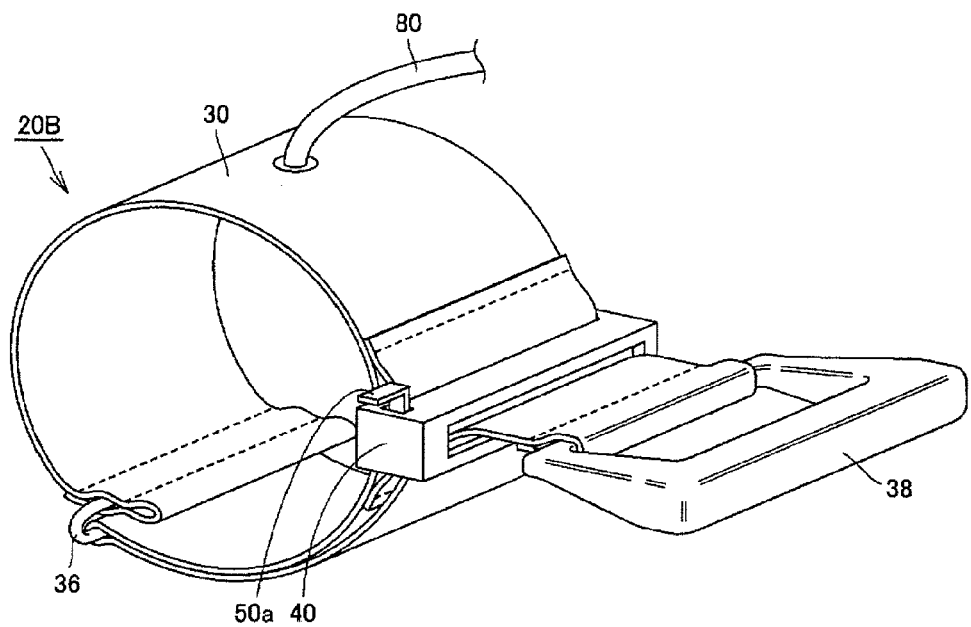
FIG. 9 is a perspective view showing an outer appearance structure of a cuff for a sphygmomanometer according to a second embodiment of the present invention.
Figure 10A:
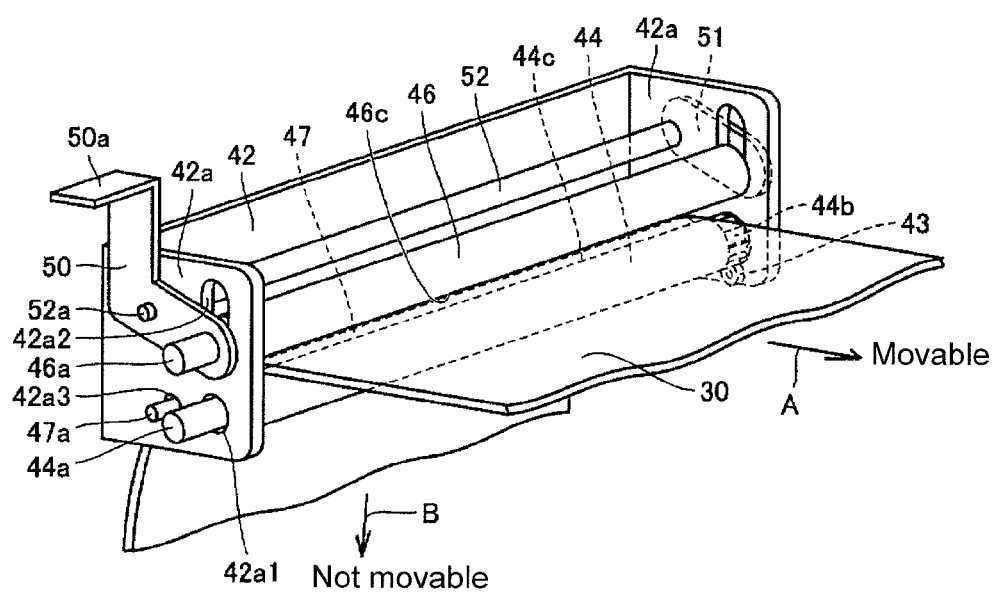
FIG. 10A is a schematic perspective view describing the configuration and the operation of the fixing mechanism of the cuff for the sphygmomanometer according to the second embodiment of the present invention.
Figure 10B:
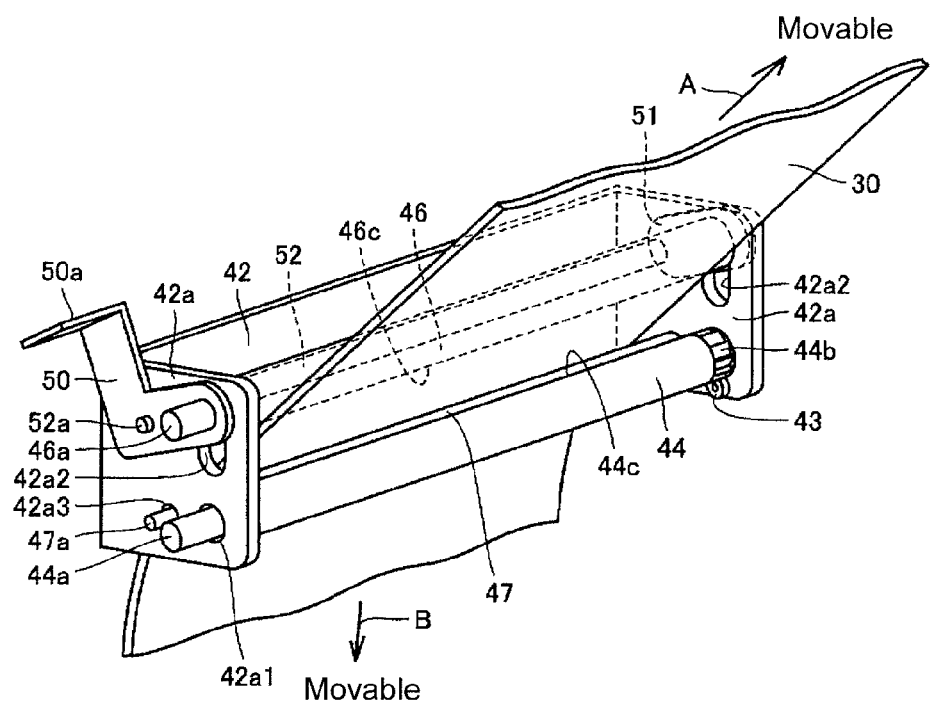
FIG. 10B is a schematic perspective view describing the configuration and the operation of the fixing mechanism of the cuff for the sphygmomanometer according to the second embodiment of the present invention.

FIG. 9 is a perspective view showing an outer appearance structure of a cuff for a sphygmomanometer according to a second embodiment of the present invention, and FIG. 10A and FIG. 10B are schematic perspective views describing the configuration and the operation of a fixing mechanism of the cuff for the sphygmomanometer according to the present embodiment. The cuff for the sphygmomanometer according to the present embodiment has a configuration similar to the cuff for the sphygmomanometer according to the first embodiment of the present invention other than the aspect described below, and the configuration of the sphygmomanometer equipped with the cuff for the sphygmomanometer according to the present embodiment is also similar to the sphygmomanometer according to the first embodiment of the present invention, and hence, the description thereof will not be repeated.

As shown in FIG. 9, FIG. 10A, and FIG. 10B, a pair of turning members 50, 51 and a shaft supporting member 52 are attached to the fixing unit 40 in a cuff 20B for a sphygmomanometer according to the present embodiment. The shaft supporting member 52 is attached so as to bridge the pair of side walls 42a of the supporting frame 42 of the fixing unit 40, and has a shaft supporting portion 52a at both ends. The shaft supporting portion 52a is positioned projecting towards the outer side from the pair of side walls 42a of the supporting frame 42, where the turning members 50, 51 are respectively fitted to the shaft supporting portions 52a. Each of the pair of turning members 50, 51 is thus turnably attached to the supporting frame 42 with the shaft supporting portion 52a of the shaft supporting member 52 as a rotation shaft.

Each of the pair of turning members 50, 51 has a predetermined position freely fitted to the shaft 46a of the stopper 46. An operation lever 50a is arranged at one turning member 50 of the pair of turning members 50, 51 so as to continuously extend from such turning member 50, which operation lever 50a reaches the exterior through an opening formed in the housing 41 of the fixing unit 40.

The pair of turning members 50, 51 and the shaft supporting member 52 correspond to a position adjustment mechanism for relatively and variably adjusting the position of the stopper 46 with respect to the roller 44 where the operation lever 50a arranged on the turning member 50 corresponds to a stopper position operating portion for variably adjusting the position of the stopper 46 through manual operation.

Specifically, as shown in FIG. 10A, a state in which the exterior cover 30 is pushed against the roller 44 is obtained when the stopper 46 is positioned proximate to the roller 44 based on the biasing force of the coil spring 45 when the operation lever 50a is not operated as shown in FIG. 10A, and a state in which the exterior cover 30 is not pushed against the roller 44 is obtained when the turning member is turned against the biasing force of the coil spring 45 so that the stopper 46 is positioned away from the roller 44 when the operation lever 50a is operated and collapsed in the horizontal direction.

Therefore, in the case of the cuff 20B for the sphygmomanometer and the sphygmomanometer equipped with the same according to the present embodiment, the fixation of the folded back portion of the exterior cover 30 with respect to the annular portion of the exterior cover 30 can be easily released by operating the operation lever 50a, so that the cuff can be attached with better operability.

Third Embodiment

Figure 11:
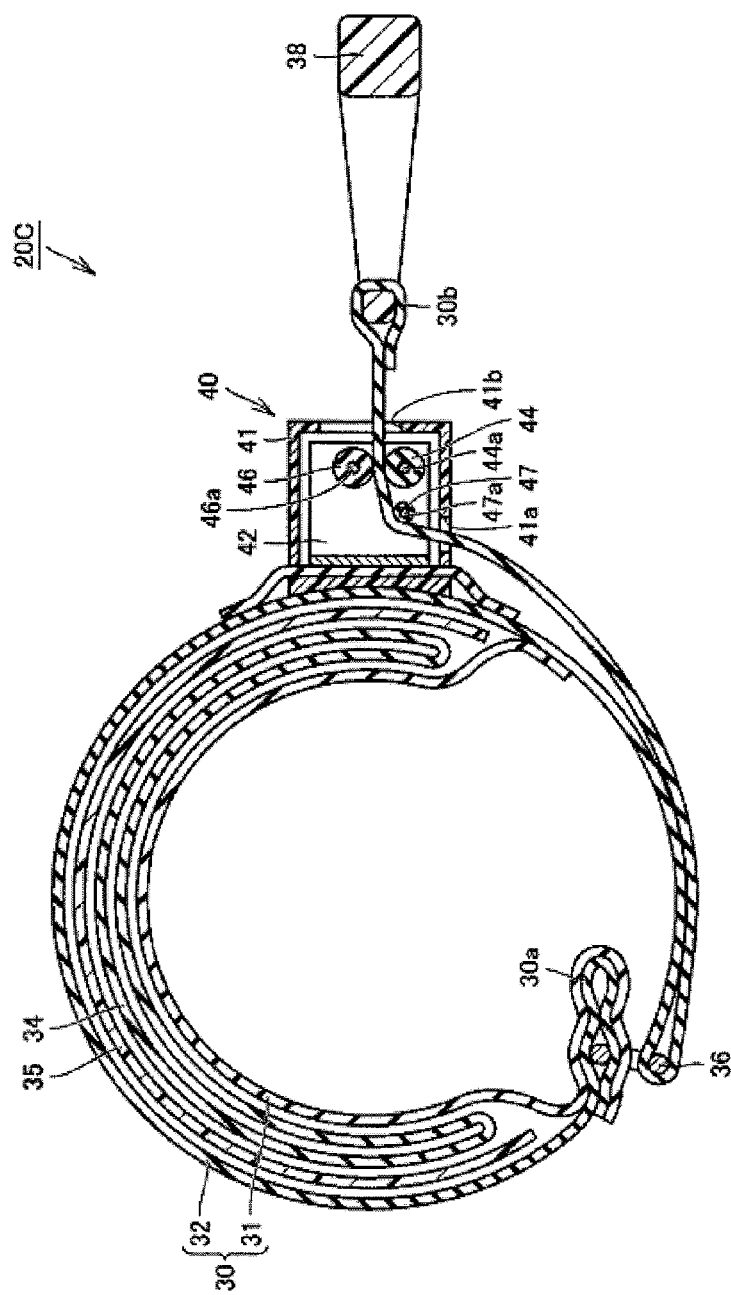
FIG. 11 is a cross-sectional view showing a detailed structure of a cuff for the sphygmomanometer according to a third embodiment of the present invention.

FIG. 11 is a schematic cross-sectional describing a detailed structure of a cuff for a sphygmomanometer according to a third embodiment of the present invention. The cuff for the sphygmomanometer according to the present embodiment has a configuration similar to the cuff for the sphygmomanometer according to the first embodiment of the present invention other than the aspect described below, and the configuration of the sphygmomanometer equipped with the cuff for the sphygmomanometer according to the present embodiment is also similar to the sphygmomanometer according to the first embodiment of the present invention, and hence, the description thereof will not be repeated.

As shown in FIG. 11, in a cuff 20C for a sphygmomanometer according to the present embodiment, a curler 35 serving as a curved elastic plate is included in the exterior cover 30 in addition to the air bladder 34. The curler 35 is arranged along the outer side of the air bladder 34, and is made from a flexible member configured so as to be elastically deformable in the radial direction by being wound to an annular form. The curler 35 may be adhered or fixed to the outer circumferential surface of the air bladder 34 through an adhesive member such as a double-sided tape, and may be configured to lie along the upper arm by maintaining its annular form thus becoming a core material of the cuff 20C.

The curler 35 is provided to facilitate the attachment when the subject attaches the cuff 20C to the upper arm, and to bias the air bladder 34 towards the upper arm side in the attachment state of the cuff 20C to the upper arm. The curler 35 is formed from a resin member such as polypropylene (PP) so as to exhibit a sufficient elastic force.

According to such configuration, not only is the air bladder 34 reliably pushed against the upper arm in the attachment state so that stable wrapping is reproduced, but a gap larger than in the case of the cuff for the sphygmomanometer having the configuration described in the first embodiment is formed between the upper arm and the annular portion of the cuff 20C by the restoration force in which the curler 35 attempts to increase the diameter when the pull tab 38 is gripped and the portion closer to the other end 30b of the exterior cover 30 is pulled downward (see FIG. 6 and description thereof) in order to detach the cuff 20C from the upper arm, and hence, the cuff 20C can be more easily detached from the upper arm.

Fourth Embodiment

Figure 12:
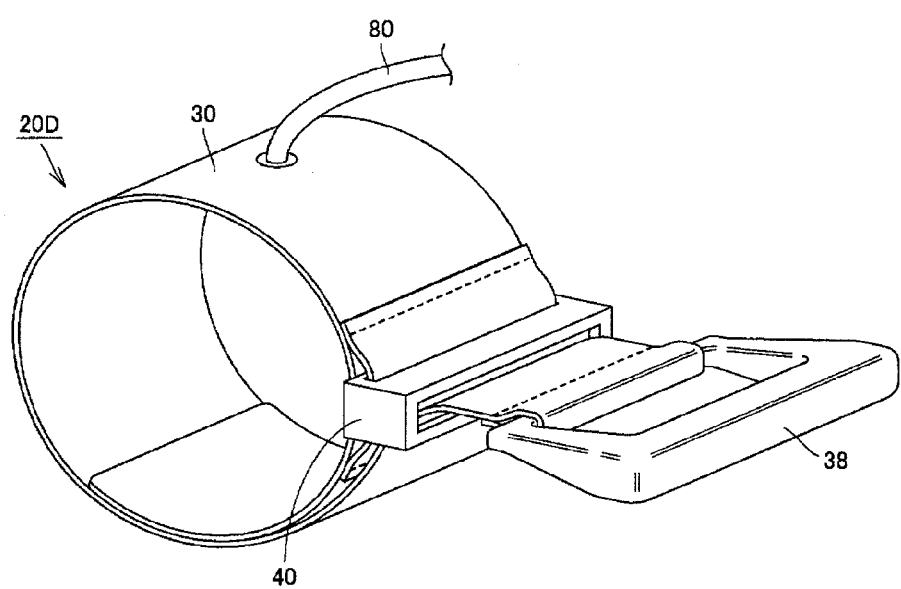
FIG. 12 is a perspective view showing an outer appearance structure of a cuff for a sphygmomanometer according to a fourth embodiment of the present invention.
Figure 13:
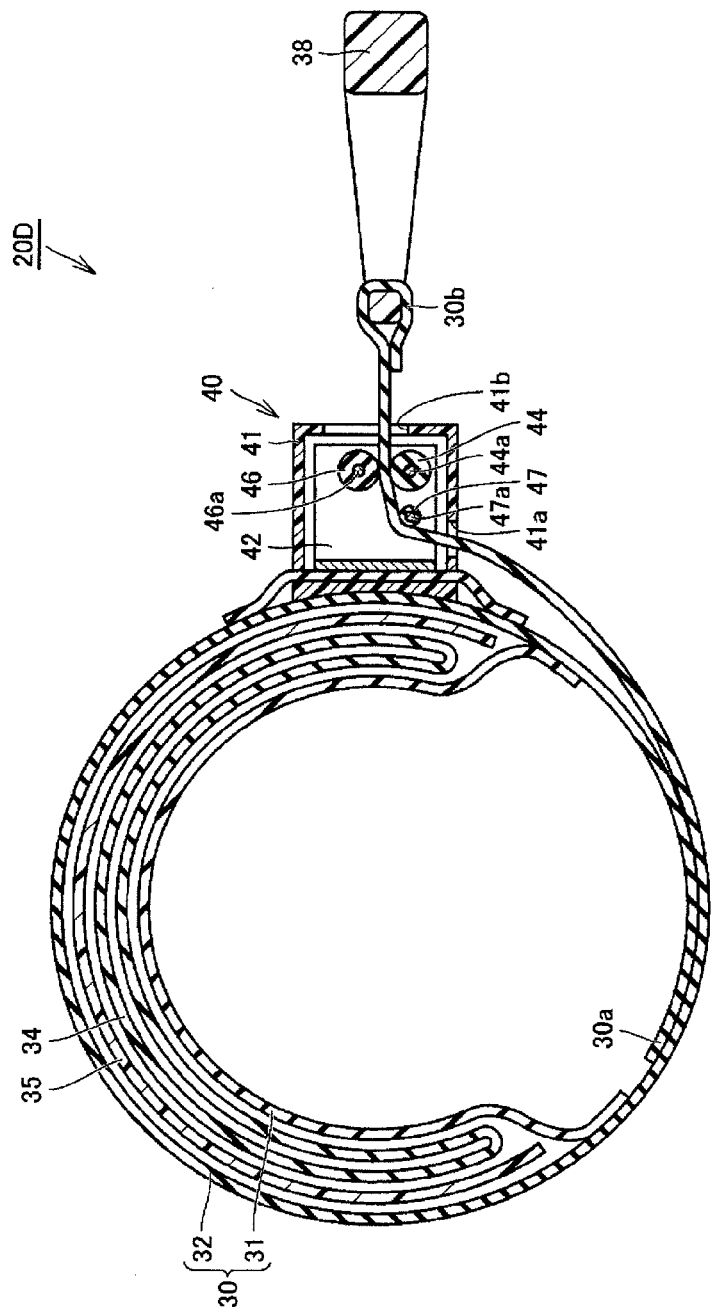
FIG. 13 is a cross-sectional view showing a detailed structure of the cuff for the sphygmomanometer according to the fourth embodiment of the present invention.

FIG. 12 is a perspective view showing an outer appearance structure of a cuff for a sphygmomanometer according to a fourth embodiment of the present invention, and FIG. 13 is a schematic cross-sectional view describing a detailed structure of the cuff for the sphygmomanometer according to the present embodiment. The cuff for the sphygmomanometer according to the present embodiment has a configuration similar to the cuff for the sphygmomanometer according to the first embodiment of the present invention other than the aspect described below, and the configuration of the sphygmomanometer equipped with the cuff for the sphygmomanometer according to the present embodiment is also similar to the sphygmomanometer according to the first embodiment of the present invention, and hence, the description thereof will not be repeated.

As shown in FIG. 12 and FIG. 13, a cuff 20D for a sphygmomanometer according to the present embodiment does not include the annular ring 36 at one end 30a of the exterior cover 30, as opposed to the cuff 20A for the sphygmomanometer according to the first embodiment described above. Instead, the curler 35, which is arranged in the cuff 20C for the sphygmomanometer according to the third embodiment, is arranged inside the exterior cover 30 in the cuff 20D for the sphygmomanometer according to the present embodiment. Therefore, in the cuff 20D for the sphygmomanometer according to the present embodiment, the annular form is maintained by the curler 35, and the portion closer to the other end 30b of the exterior cover 30 is overlapped on the annular portion of the exterior cover 30 to form an overlapping portion in the exterior cover 30. Such overlapping portion of the exterior cover 30 is inserted to the fixing unit 40.

According to the cuff 20D for the sphygmomanometer and the sphygmomanometer equipped with the same according to the present embodiment described above, effects similar to the effects described according to the first and third embodiments can be obtained.

Fifth Embodiment

According to the first embodiment of the present invention described above, a case in which the sphygmomanometer 1 is configured to carry out the process of driving the pressurization pump 17 and the like after attaching the cuff 20A to measure the blood pressure value has been illustratively described, but whether or not the wrapping state of the cuff 20A is in an optimum wrapping state can also be detected by preliminarily pressurizing the air bladder 34 slightly prior to the attachment of the cuff 20A. A case in which the sphygmomanometer is configured in such manner will be described below as a fifth embodiment.

Figure 14:
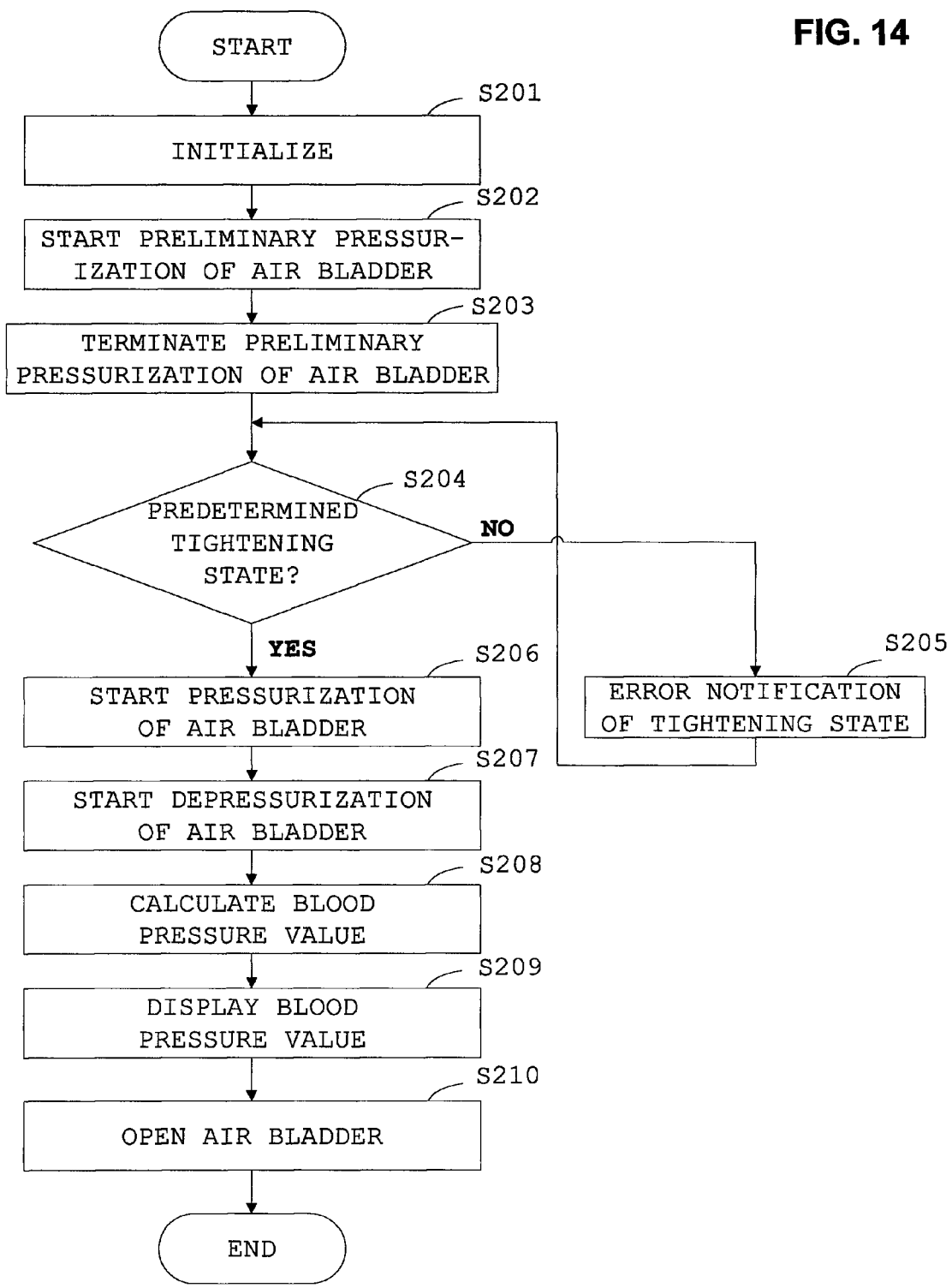
FIG. 14 is a flowchart showing a flow of processes of the sphygmomanometer according to a fifth embodiment of the present invention.

FIG. 14 is a flowchart showing a flow of processes of the sphygmomanometer according to the fifth embodiment of the present invention. The configuration of the cuff for the sphygmomanometer and the sphygmomanometer equipped with the same according to the present embodiment are similar to that of the sphygmomanometer according to the first embodiment of the present invention described above, and hence, the description thereof will not be repeated.

As shown in FIG. 14, in the sphygmomanometer according to the present embodiment, the operation unit 14 arranged on the main body 10 is first operated to turn ON the power of the sphygmomanometer prior to the attachment of the cuff 20A. The power serving as the power supply is thereby supplied from the power supply unit 15 to the control unit 11 to drive the control unit 11, and the sphygmomanometer is initialized (step S201). After the initialization, the control unit 11 closes the exhaust valve 18 and drives the pressurization pump 17, and starts the preliminary pressurization of the air bladder 34 (step S202). After a predetermined volume of air is introduced to the air bladder 34, the control unit 11 stops the drive of the pressurization pump 17 and terminates the preliminary pressurization (step S203).

The control unit 11 then determines whether or not the cuff 20A is in a predetermined tightening state based on the signal input from the oscillation circuit 19a. The determination of whether or not the cuff 20A is in the predetermined tightening state made in the control unit 11 is made based on whether or not the signal input from the oscillation circuit 19a has reached a predetermined threshold value or higher by using the fact that the inner pressure of the air bladder 34 reaches a predetermined pressure if the cuff 20A is attached to the upper arm in a fitted manner.

The control unit 11 carries out an error display on the display unit 13 (step S205) when determined that the cuff 20A is not in the predetermined tightening state (NO in step S204), and again returns to step S204 to determine whether or not the cuff 20A is in the predetermined tightening state.

The subject performs the attachment operation of the cuff 20A during the determination by the control unit 11. Specifically, with reference to the display of the display unit 13, the pull tab 38 of the cuff 20A is pulled to reduce the diameter of the annular portion of the cuff 20A, and the tightening operation is performed until the error display disappears so that the cuff 20A is fitted to the upper arm without any gap.

The control unit 11 starts the drive of the pressurization pump 17 and gradually raises the cuff pressure of the air bladder 34 (step S206) when determined that the cuff 20A is in the predetermined tightening state (YES in step S204), stops the pressurization pump 17 when the cuff pressure reaches a predetermined level for blood pressure value measurement, gradually opens the closed exhaust valve 18 to gradually exhaust the air in the air bladder 34 and gradually depressurize the cuff pressure (step S207), and measures the blood pressure value in the micro-speed depressurization process of the cuff pressure.

Then, the control unit 11 calculates the blood pressure value such as the systolic blood pressure value and the diastolic blood pressure value through a known procedure (step S208), displays the blood pressure value serving as the measurement result on the display unit 13 (step S209) and also stores the blood pressure value in the memory unit 12, opens the air bladder 34 to completely exhaust the air in the air bladder 34 (step S210), and waits for the command to turn OFF the power by the subject to terminate the operation.

According to the sphygmomanometer following the processing procedure described above, the blood pressure value measurement is carried out only after the cuff 20A is wrapped around the upper arm in a fitted state, and hence, a sphygmomanometer enabling highly accurate blood pressure value measurement can be realized.

According to the first to fifth embodiments of the present invention described above, a case in which the surface of the roller is covered with a rubber material or a case in which irregularities are formed on the surface of the roller has been described illustratively, but it does not necessarily need to be configured in such manner, and the surface of the roller may be covered with a member other than the rubber material, or the irregularities do not need to be particularly formed on the surface of the roller as long as a friction force of merely fixing the exterior cover is generated between the surface of the exterior cover and the surface of the roller.

Further, according to the first to fifth embodiments of the present invention described above, a case in which the stopper is not only movably supported but also rotatably supported by the supporting frame has been described illustratively, but the stopper does not necessarily need to be rotatably supported by the supporting frame, and may be non-rotatably supported by the supporting frame. If the stopper is rotatably supported by the supporting frame, the stopper may be supported so as to be rotatable only in one direction, similar to the case of the roller. The rotating direction of the stopper in this case is, similar to the case of the roller, the direction where the size of the annular portion of the exterior cover is reduced in a state where the overlapping portion of the exterior cover is sandwiched between the stopper and the roller.

Further, according to the first to fifth embodiments of the present invention described above, a case in which the stopper is movable supported by the supporting frame has been described by way of example, but the stopper is immovably fixed to the supporting frame and the roller is movably fixed to the supporting frame if a configuration in which some kind of release member is arranged is adopted. In other words, if the release member is arranged, at least one of the roller and the stopper merely needs to be movably configured.

Further, according to the first to fifth embodiments of the present invention described above, a case in which a configuration using a clutch plate and a clutch nail that gears with the clutch plate is used for the one way clutch has been described, but the one way clutch of other configurations may obviously be used. For example, a bearing form may be used for the one way clutch of other configurations. The one way clutch of the bearing form includes an outer ring to be externally inserted with respect to the shaft and a roller and a spring arranged between the outer ring and the shaft, where when the outer ring is rotated towards a predetermined direction, for example, the roller gears with both the outer ring and the shaft by the action of the spring so that the shaft is driven and rotated towards the same direction, whereas when the outer ring is rotated in a direction opposite to the predetermined direction, the roller idles away from either the outer ring or the shaft.

Further, according to the first to fifth embodiments of the present invention described above, a so-called upper arm type sphygmomanometer in which the cuff is attached to the upper arm when measuring the blood pressure value and a cuff for a sphygmomanometer arranged therein have been described by way of example, but are not particularly limited thereto, and one or more embodiments of the present invention may, of course, be applied to a so-called wrist type sphygmomanometer in which the cuff is attached to the wrist when measuring the blood pressure value and a cuff for a sphygmomanometer arranged therein, or a so-called ankle type sphygmomanometer in which the cuff is attached to the ankle when measuring the blood pressure value and a cuff for a sphygmomanometer arranged therein.

Further, according to the first to fifth embodiments of the present invention described above, a case in which one or more embodiments of the present invention are applied to a sphygmomanometer capable of measuring the blood pressure value such as the systolic blood pressure value and the diastolic blood pressure value and a cuff for a sphygmomanometer arranged therein has been described by way of example, but one or more embodiments of the present invention can also be applied to a blood pressure information measurement device capable of measuring other blood pressure information (e.g., average blood pressure value, pulse wave, pulse, AI value, etc.) other than the blood pressure value such as the systolic blood pressure value and the diastolic blood pressure value and a cuff for a blood pressure information measurement device arranged therein.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

DESCRIPTION OF REFERENCE NUMERALS 1 sphygmomanometer
10 main body
11 control unit
12 memory unit
13 display unit
14 operation unit
15 power supply unit
16 air system component
17 pressurization pump
17a pressurization pump drive circuit
18 exhaust valve
18a exhaust valve drive circuit
19 pressure sensor
19a oscillation circuit
20A to 20D cuff
30 exterior cover
30a one end
30b other end
31 inner side cover
32 outer side cover
34 air bladder
35 curler
36 annular ring
38 pull tab
40 fixing unit
41 housing
41a, 41b opening
42 supporting frame
42a side wall
42a1 to 42a3 shaft supporting hole
43 clutch nail
44 roller
44a shaft
44b clutch plate
44c surface
45 coil spring
46 stopper
46a shaft
46c surface
47 driven roller
47a shaft
48 pushing member (release member)
50, 51 turning member
50a operation lever
52 shaft supporting member
52a shaft supporting portion
80 air tube

The invention claimed is:

1. A cuff for a blood pressure information measurement device comprising:
a fluid bladder that is configured to compress a living body;
a band-shaped exterior cover that comprises:
an annular portion to be wrapped around the living body;
an overlapping portion to be overlapped on the annular portion; and
the fluid bladder;
a flexible curved elastic plate that is included in the exterior cover so as to be positioned along an outer side of the fluid bladder, and that is elastically deformable along a radial direction of the annular portion of the exterior cover; and
a fixing mechanism that fixes the overlapping portion of the exterior cover to the annular portion of the exterior cover,
wherein the fixing mechanism comprises:
a roller rotatable only in one direction;
a stopper facing the roller; and
a pushing mechanism that pushes the stopper towards the roller,
wherein the overlapping portion of the exterior cover is:
inserted between the roller and the stopper, and the stopper is pushed towards the roller by the pushing mechanism so as to be pushed against a surface of the roller; and
fixed to the annular portion of the exterior cover by a friction force generated with the roller,
wherein a release mechanism that releases the fixing of the overlapping portion of the exterior cover to the annular portion of the exterior cover by separating the roller and the stopper is further arranged, and
wherein the roller is rotatable only in a direction of reducing a size of the annular portion of the exterior cover when the overlapping portion of the exterior cover is sandwiched between the roller the stopper.

2. The cuff for the blood pressure information measurement device according to claim 1, wherein the pushing mechanism comprises a spring that biases the stopper towards the roller.

3. The cuff for the blood pressure information measurement device according to claim 1, wherein the pushing mechanism comprises a member made from a shape memory alloy that contracts in a conduction state and extends in a non-conduction state.

4. The cuff for the blood pressure information measurement device according to claim 1,
wherein the release mechanism comprises a position adjustment mechanism that relatively and variably adjusts the position of the stopper with respect to the roller, and
wherein the position adjustment mechanism comprises a manually operable stopper position operating portion.

5. The cuff for the blood pressure information measurement device according to claim 1, further comprising:
a hook member, arranged at one end in a longitudinal direction of the exterior cover, that maintains the exterior cover in an annular form by being inserted with another end in the longitudinal direction of the exterior cover and enabling a portion closer to the other end of the exterior cover to be folded back along a circumferential direction of the annular portion of the exterior cover,
wherein the overlapping portion of the exterior cover comprises the exterior cover of the portion folded back using the hook member.

6. A blood pressure information measurement device comprising:

the cuff for the blood pressure information measurement device according to claim 1;

an expansion/contraction mechanism that expands and contracts the fluid bladder; and a blood pressure information acquiring unit that acquires blood pressure information.

* * * * *